(12) United States Patent
Zhang et al.

(10) Patent No.: US 10,850,101 B2
(45) Date of Patent: Dec. 1, 2020

(54) ANATOMICAL TARGETING OF NEUROMODULATION

(71) Applicant: Boston Scientific Neuromodulation Corporation, Valencia, CA (US)

(72) Inventors: Tianhe Zhang, Studio City, CA (US); Bradley Lawrence Hershey, Valencia, CA (US); Michael A. Moffitt, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 459 days.

(21) Appl. No.: 15/710,190

(22) Filed: Sep. 20, 2017

(65) Prior Publication Data

US 2018/0085583 A1  Mar. 29, 2018

Related U.S. Application Data

(60) Provisional application No. 62/400,472, filed on Sep. 27, 2016.

(51) Int. Cl.
  *A61N 1/36* (2006.01)
  *G16H 50/50* (2018.01)
  *A61N 1/372* (2006.01)

(52) U.S. Cl.
  CPC ....... *A61N 1/36057* (2013.01); *A61N 1/3605* (2013.01); *A61N 1/36062* (2017.08);
  (Continued)

(58) Field of Classification Search
  CPC ............ A61N 1/37247; A61N 1/36185; A61N 1/36062; A61N 1/3605; A61N 1/36057
  See application file for complete search history.

(56) References Cited

U.S. PATENT DOCUMENTS 7,333,857 B2 * 2/2008 Campbell .......... A61N 1/36071
                                            607/117
8,412,345 B2   4/2013 Moffitt
               (Continued)

FOREIGN PATENT DOCUMENTS

WO    WO-2018063879 A1   4/2018

OTHER PUBLICATIONS

"Medtronic Programming Guide, Neurostimulators for Chronic Pain", UC201203811a EN @ 2013 Medtronic, Inc., 1-130.
(Continued)

*Primary Examiner* — Rex R Holmes
*Assistant Examiner* — Sana Sahand
(74) *Attorney, Agent, or Firm* — Schwegman Lundberg & Woessner, P.A.

(57) ABSTRACT

A neuromodulation targeting system includes a GUI that facilitates selection of one or more neuromodulation target regions. The GUI provides an interactive display representing anatomy of a patient with user-selectable portions corresponding to a plurality of predefined anatomical regions associated with distinct localized clinical effects of neuromodulation. The system further includes a targeting selector engine that is responsive to user selection of a first portion of the interactive display by configuring delivery of neuromodulation therapy to a first target region to produce a first localized clinical effect in the patient at a location corresponding to the first portion of the display, upon administration of the neuromodulation therapy to the patient.

20 Claims, 20 Drawing Sheets

(52) U.S. Cl.
CPC ..... *A61N 1/36071* (2013.01); *A61N 1/36092* (2013.01); *A61N 1/36103* (2013.01); *A61N 1/36132* (2013.01); *A61N 1/36185* (2013.01); *A61N 1/37247* (2013.01); *G16H 50/50* (2018.01)

(56) References Cited

U.S. PATENT DOCUMENTS

| | | | |
|---|---|---|---|
| 8,909,350 B2 | 12/2014 | Lee | |
| 8,918,177 B2* | 12/2014 | Gauthier | A61N 1/37247 607/46 |
| 9,044,610 B2 | 6/2015 | Rosenberg et al. | |
| 9,737,715 B2* | 8/2017 | Moffitt | A61N 1/36132 |
| 10,076,664 B1* | 9/2018 | Thacker | A61N 1/37264 |
| 2007/0203544 A1 | 8/2007 | Goetz et al. | |
| 2008/0064947 A1* | 3/2008 | Heruth | A61B 90/36 600/407 |
| 2012/0083857 A1* | 4/2012 | Bradley | A61N 1/36175 607/46 |
| 2012/0239109 A1* | 9/2012 | Lee | A61N 1/36185 607/45 |
| 2012/0265268 A1* | 10/2012 | Blum | A61N 1/36021 607/46 |
| 2013/0060300 A1* | 3/2013 | Polefko | A61N 1/36071 607/46 |
| 2014/0155953 A1* | 6/2014 | Wacnik | A61N 1/36185 607/46 |
| 2016/0082252 A1 | 3/2016 | Hershey et al. | |
| 2016/0228706 A1 | 8/2016 | Hershey et al. | |
| 2019/0009094 A1 | 1/2019 | Zhang et al. | |

OTHER PUBLICATIONS

Howell, Bryan, et al., "Evaluation of Intradural Stimulation Efficiency and Selectivity in a Computational Model of Spinal Cord Stimulation", PLOS One; DOI:10.1371/journal.pone.0114938, (Dec. 23, 2014), 1-25.

"U.S. Appl. No. 16/027,040, Non Final Office Action dated Feb. 6, 2020", 10 pgs.

"European Application Serial No. 1777752.1, Response to Communication pursuant to Rules 161 and 162 filed Dec. 4, 2019", 9 pgs.

"International Application Serial No. PCT/US2017/052440, International Preliminary Report on Patentability dated Apr. 11, 2019", 8 pgs.

"International Application Serial No. PCT/US2017/052440, International Search Report dated Dec. 15, 2017", 3 pgs.

"International Application Serial No. PCT/US2017/052440, Written Opinion dated Dec. 15, 2017", 6 pgs.

* cited by examiner

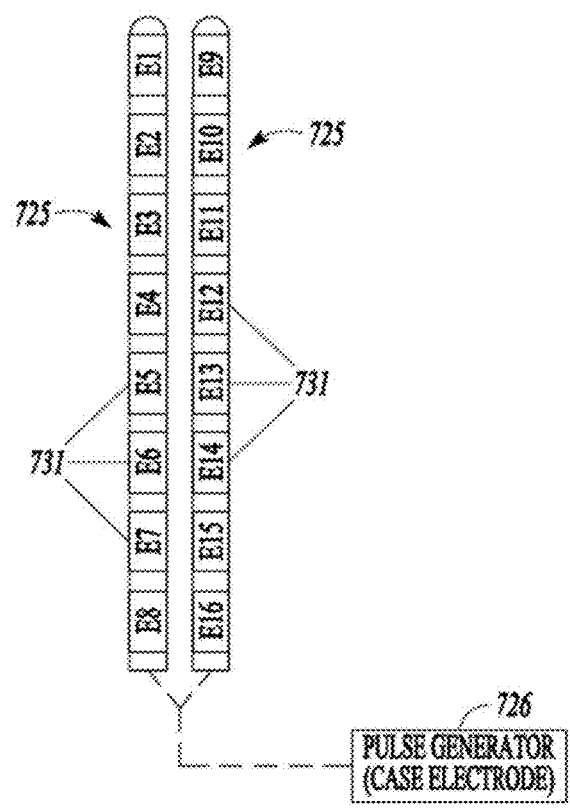
FIG. 7
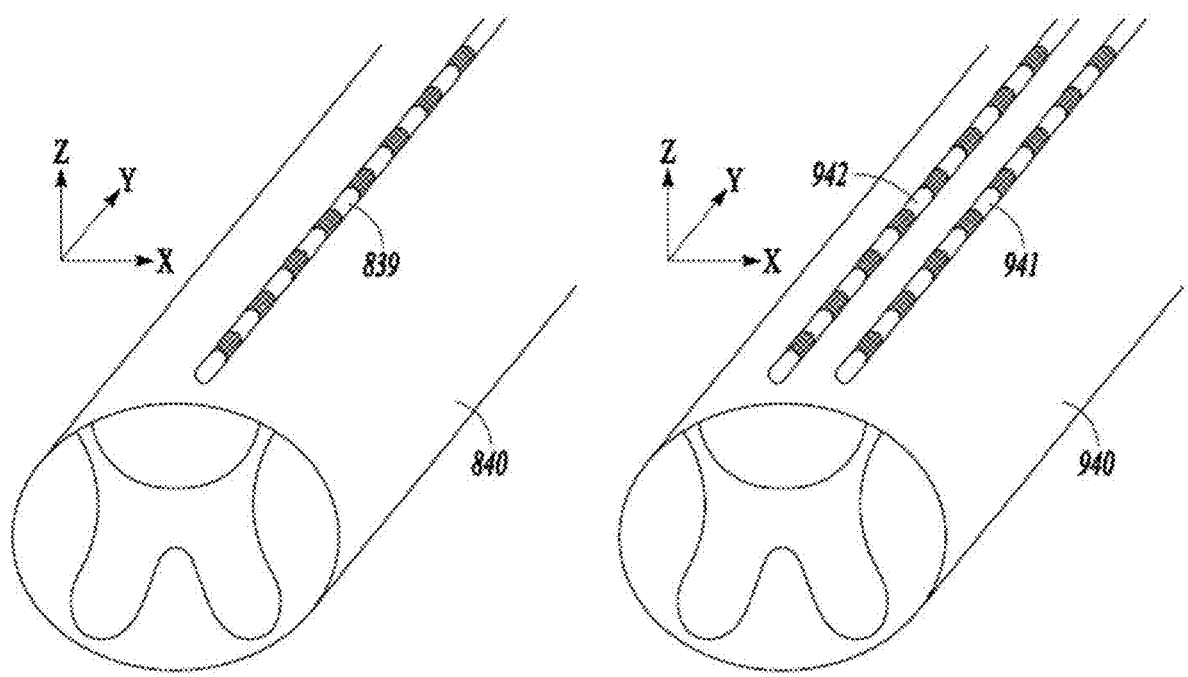
FIG. 8  FIG. 9

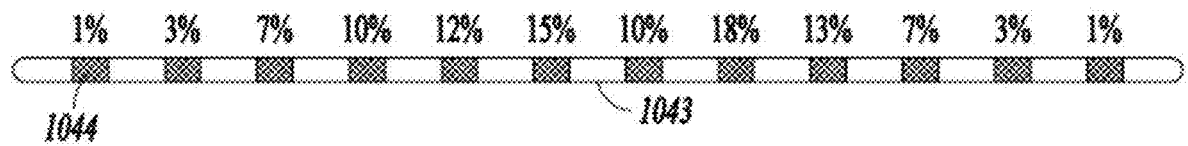
*FIG. 10*
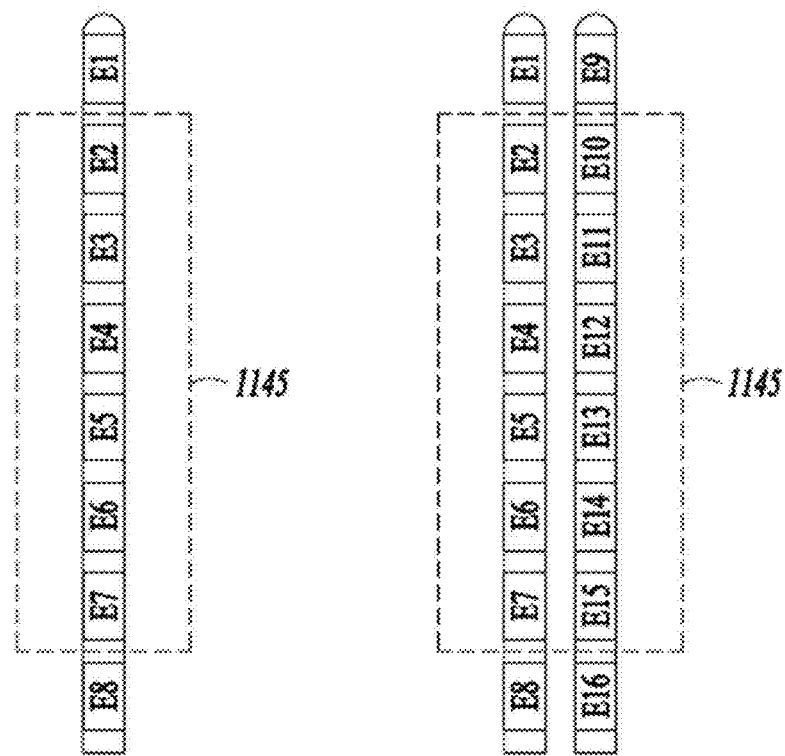
*FIG. 11A*     *FIG. 11B*

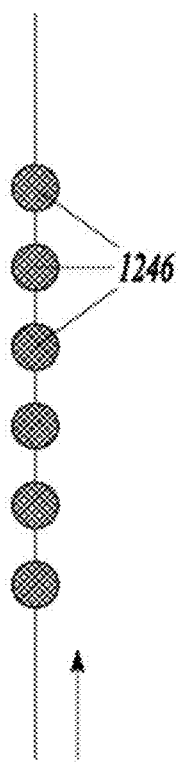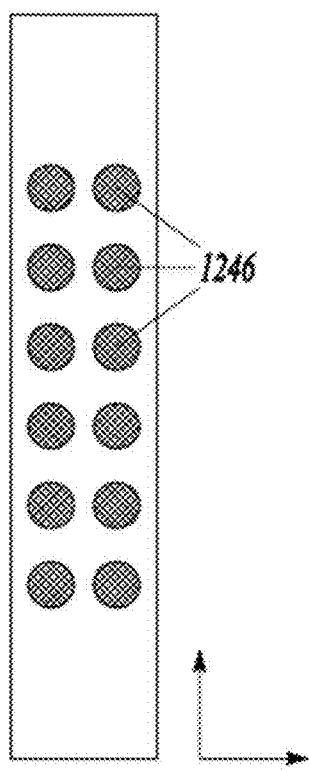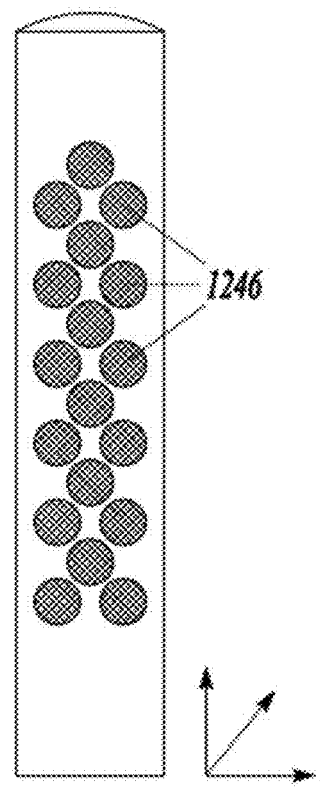
*FIG. 12A*          *FIG. 12B*          *FIG. 12C*

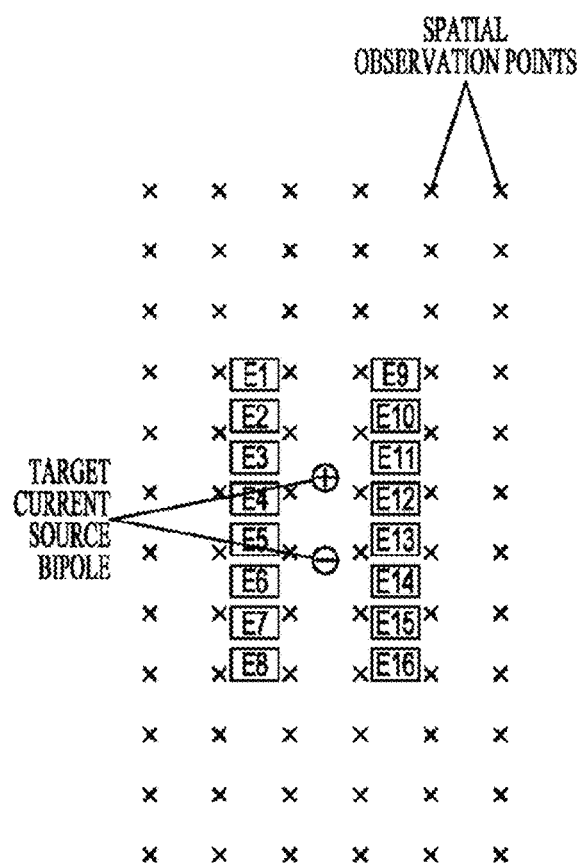 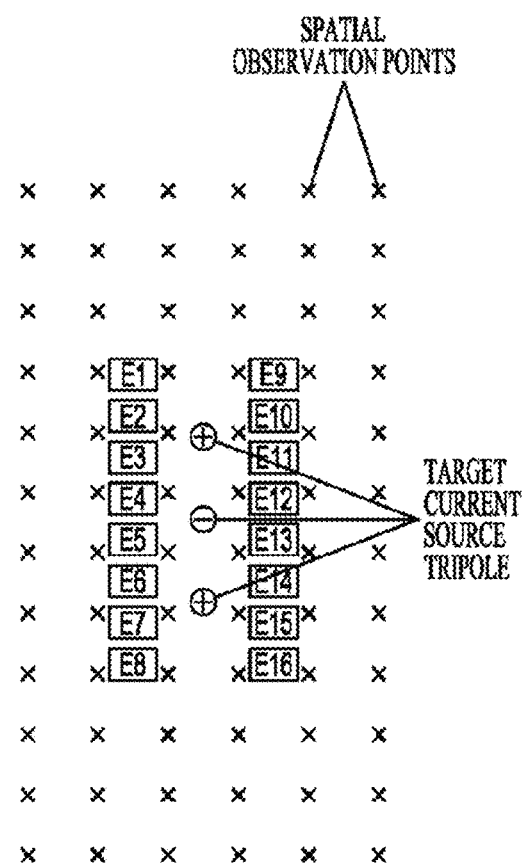
*FIG. 25A*  *FIG. 25B*

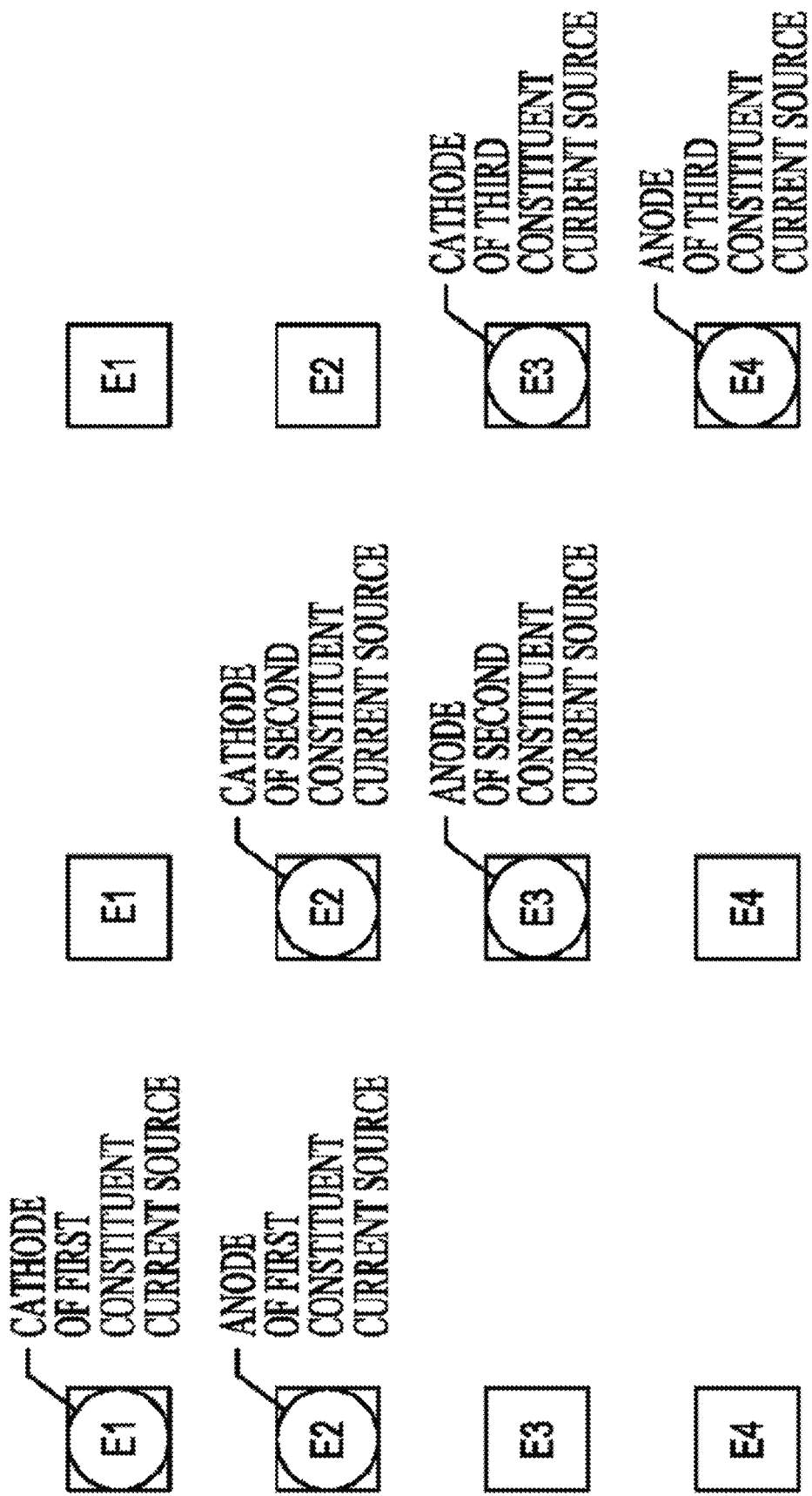

ANATOMICAL TARGETING OF NEUROMODULATION

CLAIM OF PRIORITY

This application claims the benefit of priority under 35 U.S.C. § 119(e) of U.S. Provisional Patent Application Ser. No. 62/400,472, filed on Sep. 27, 2016, which is incorporated by reference into the present disclosure in its entirety.

TECHNICAL FIELD

This document relates generally to medical devices, and more particularly, to systems, devices and methods for delivering neuromodulation.

BACKGROUND

Neuromodulation (or "neural neuromodulation", also referred to as "neurostimulation" or "neural stimulation") has been proposed as a therapy for a number of conditions. Often, neuromodulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes.

Conventional SCS delivers electrical pulses to the dorsal column fibers in the dorsal aspect of the spinal cord, which in turn activate a set of inhibitory neurons in the dorsal horn, thereby masking the transmission of pain signals from the periphery of the body to the brain. Notably, the dorsal column fibers are organized in a spatially-dependent manner according to the region of the body with which they respectively interface. Accordingly, it is desirable to optimally target the neuromodulation to the precise fibers that correspond to the source of pain to be treated, while minimizing stimulation of other fibers in order to reduce or avoid side-effects.

However, it can be a challenge to find a desirable or optimal location (sweet-spot) for the neuromodulation field during programming of a neuromodulation device. Optimal-location searching has traditionally been an ad-hoc, trial-and-error, process by which a healthcare professional adjusts the targeting of the neuromodulation to provide optimal pain relief for the patient with minimal discomfort. Typically, the patient provides feedback to the healthcare provider by identifying locations of pain or discomfort to be relieved by the neuromodulation. Although this type of feedback may indicate the need for adjustment of the neuromodulation targeting, finding the correct targeting location is not always a simple matter of steering the neuromodulation towards the location of the pain. This is due in large part to the complexity of the anatomy, including the natural location-based variation of fiber diameter, which tends to respond differently to different neurostimulation parameters.

These challenges are compounded in sub-perception (i.e., non-paresthetic) neuromodulation applications, where the "settling time" for a patient to recognize and assess the efficacy of a targeted neuromodulation administration is significantly longer than in the case of paresthetic treatment.

SUMMARY

The following examples illustrate various aspects of the embodiments described herein.

Example 1 is a neuromodulation targeting system facilitating spatial selection of a neuromodulation objective, the system comprising: a graphical user interface (GUI) that includes an interactive display representing anatomy of a patient with user-selectable anatomic-specific inputs associated with a plurality of predefined neural pathways corresponding to distinct localized clinical effects of neuromodulation; and a targeting selector engine operatively coupled with the GUI, the targeting selector engine being responsive to user selection of a first anatomic-specific input to: computationally determine a first target region where neuromodulation therapy is to be directed, the first target region being distinct from an anatomic location of the anatomic-specific input, and configure delivery of the neuromodulation therapy to the first target region to produce a first localized clinical effect in the patient at a location corresponding to the first anatomic-specific input, upon administration of the neuromodulation therapy to the patient, to achieve the neuromodulation objective.

In Example 2, the subject matter of Example 1 optionally includes wherein the first target region is a neuroanatomic region selected from the group consisting of: a dorsal column region, a dorsal root region, a dorsal horn region, a dermatomic region, or any combination thereof.

In Example 3, the subject matter of any one or more of Examples 1-2 optionally include wherein the plurality of predefined neural pathways corresponding to distinct localized clinical effects of neuromodulation include dermatomes.

In Example 4, the subject matter of any one or more of Examples 1-3 optionally include wherein the first anatomic-specific input represents a site where pain is reported by the patient.

In Example 5, the subject matter of any one or more of Examples 1-4 optionally include wherein the interactive display representing anatomy of the patient includes a dermatomal map of the patient with individually-selectable dermatomes.

In Example 6, the subject matter of any one or more of Examples 1-5 optionally include wherein the interactive display representing anatomy of the patient further includes a spinal map of the patient with selectable portions of dorsal roots.

In Example 7, the subject matter of any one or more of Examples 1-6 optionally include wherein the interactive display representing anatomy of the patient includes a map of fiber tracts proximate the spinal cord with selectable portions of the fiber tracts.

In Example 8, the subject matter of any one or more of Examples 1-7 optionally include wherein the interactive display representing the anatomy of the patient is based on actual measured anatomic characteristics of the patient.

In Example 9, the subject matter of any one or more of Examples 1-8 optionally include wherein the interactive display further includes a therapy type selector input facilitating selection of neuromodulation type from among paresthesia neuromodulation, and sub-perception neuromodulation.

In Example 10, the subject matter of Example 9 optionally includes wherein the interactive display further facilitates selection of an exclusion zone of the anatomy of the patient that is to be free of neuromodulation.

In Example 11, the subject matter of any one or more of Examples 1-10 optionally include an electrotherapy parameter selector engine configured to determine an electrical signal waveform to be applied to the first target region, the electrical signal waveform being specific to a neurologic structure present at the first target region.

In Example 12, the subject matter of Example 11 optionally includes wherein the electrotherapy parameter selector engine is further configured to determine the electrical signal waveform based on an activation function associated with the neurologic structure at the first target region.

In Example 13, the subject matter of Example 12 optionally includes wherein the electrotherapy parameter selector engine is configured to determine the electrical signal waveform based on an orientation of the neurologic structure at the first target region relative to a location of a set of electrodes from which the neuromodulation therapy is to be directed.

In Example 14, the subject matter of any one or more of Examples 11-13 optionally include wherein the GUI includes a treatment objective input to accept a clinical effect objective specified by a user; and wherein the electrotherapy parameter selector engine is further configured to determine the electrical signal waveform based on the clinical effect objective.

In Example 15, the subject matter of any one or more of Examples 1-14 optionally include wherein the first localized clinical effect includes pain relief.

Example 16 is in a neuromodulation targeting system, a method for facilitating spatial selection of a neuromodulation objective, the method comprising: providing a graphical user interface (GUI) that includes an interactive display representing anatomy of a patient with user-selectable anatomic-specific inputs associated with a plurality of pre-defined neural pathways corresponding to distinct localized clinical effects of neuromodulation; and responding to user selection of a first anatomic-specific input, including: computationally determining a first target region where neuromodulation therapy is to be directed, the first target region being distinct from an anatomic location of the anatomic-specific input, and configuring the neuromodulation therapy for delivery to the first target region to produce a first localized clinical effect in the patient at a location corresponding to the first anatomic-specific input, upon administration of the neuromodulation therapy to the patient, to achieve the neuromodulation objective.

In Example 17, the subject matter of Example 16 optionally includes determining an electrical signal waveform to be applied to the first target region, the electrical signal waveform being specific to a neurologic structure present at the first target region.

In Example 18, the subject matter of Example 17 optionally includes determining the electrical signal waveform based on an activation function associated with the neurologic structure at the first target region.

In Example 19, the subject matter of Example 18 optionally includes determining the electrical signal waveform based on an orientation of the neurologic structure at the first target region relative to a location of a set of electrodes from which the neuromodulation therapy is to be directed.

In Example 20, the subject matter of any one or more of Examples 17-19 optionally include wherein the GUI includes a treatment objective input to accept a clinical effect objective specified by a user; further comprising: determining the electrical signal waveform based on the clinical effect objective.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 7 illustrates, by way of example, some features of the neuromodulation leads and a pulse generator.

FIG. 8 is a schematic view of a single electrical neuromodulation lead implanted over approximately the longitudinal midline of the patient's spinal cord.

FIG. 9 illustrates an embodiment where an electrical neuromodulation lead has been implanted more laterally with respect to the spinal cord, thereby placing it proximate the dorsal horn of the spinal cord, and the other electrical neuromodulation lead has been implanted more medially with respect to the spinal cord, thereby placing it proximate the dorsal column of the spinal cord.

FIG. 10 illustrates a schematic view of the electrical neuromodulation lead showing an example of the fractionalization of the anodic current delivered to the electrodes on the electrical neuromodulation lead.

FIGS. 11A-11B illustrate, by way of example and not limitation, electrode arrangements and test regions of neural tissue along the electrode arrangements.

FIGS. 12A-12C illustrate, by way of example and not limitation, neural tissue locations that may be targeted within the test region in one, two and three dimensions, respectively.

FIGS. 25A-25B, are operational diagrams illustrating examples of the functionality of a neuromodulation delivery controller mapping a target electrical field to the electrode array by estimating the field potential values, an activating function, for example, according to embodiments.

FIGS. 26A-26C are diagrams illustrating operation of a neuromodulation delivery controller to automatically select a plurality of constituent current sources at the locations of the electrodes, according to an example embodiment.

DETAILED DESCRIPTION

Figure 1:
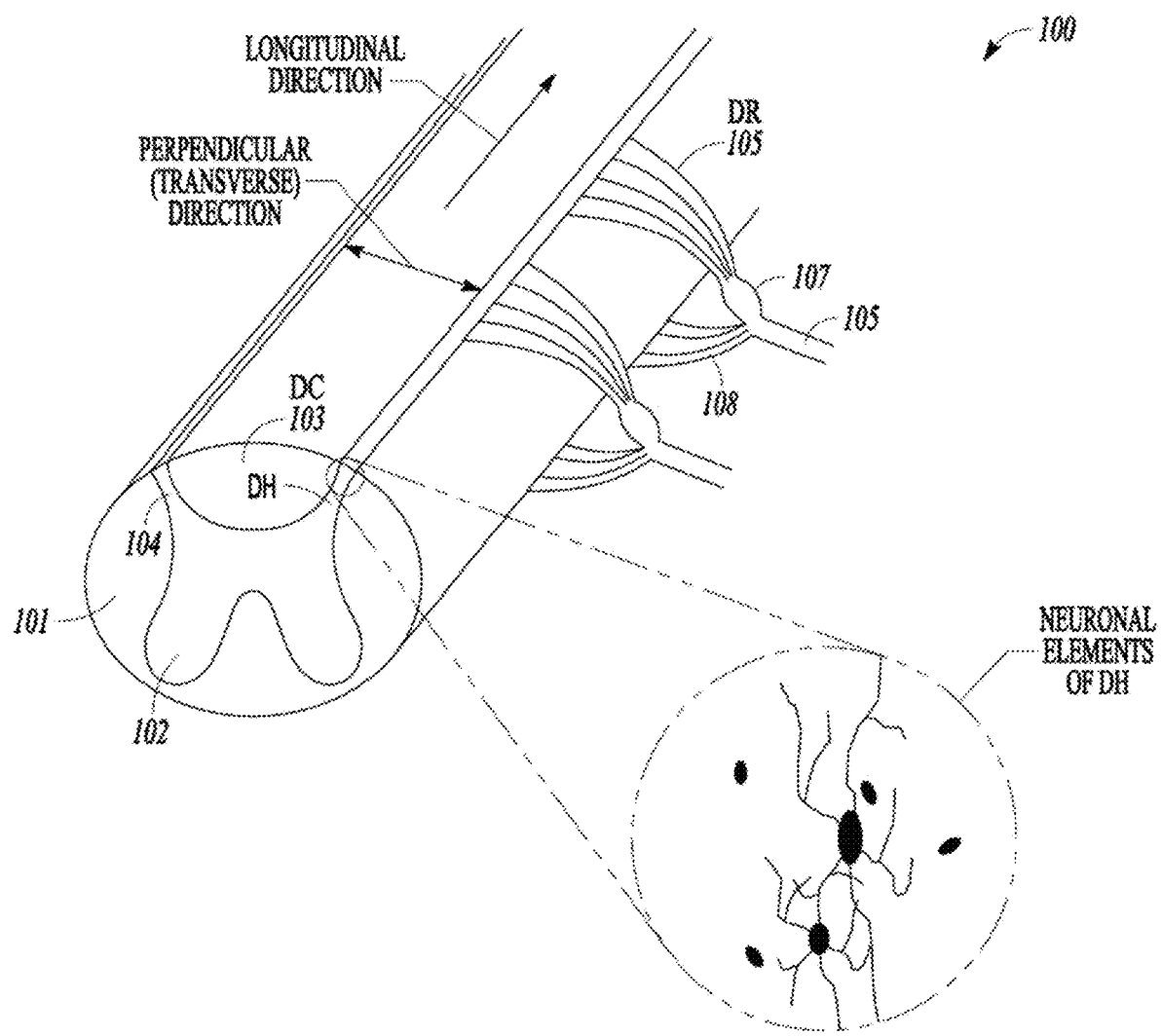
FIG. 1 illustrates a portion of a spinal cord.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Sub-perception neuromodulation is neuromodulation that can be therapeutically effective. Thus, the therapeutic effects of the sub-perception neuromodulation can be perceived. However, unlike conventional SCS therapy which can cause sensations (e.g. paresthesia) when the therapy is delivered, the energy of the delivered sub-perception neuromodulation field is not perceptible apart from any perceptible therapeutic effects.

Sub-perception SCS may typically have a wash-in period on the order of about one day. Thus, when the programmed neuromodulation parameters are changed to change the location of the neuromodulation field, the patient may not be able to determine the effect that the changes have on pain for a day or so. This makes it difficult quickly titrate the neuromodulation field of the sub-perception SCS to provide effective pain relief to the patient.

Various embodiments may be used to provide a faster therapeutic response (e.g. pain relief) to the sub-perception neuromodulation. Faster responses to sub-perception neuromodulation may be useful in order to find an effective location (sweet-spot) for the neuromodulation field within an office visit. The sweet spot may be a relatively optimal location for the neuromodulation field as it is more optimal than other locations tested.

Various embodiments may deliver a low intensity field in preparation for testing for and finding the sweet-spot for the sub-perception neuromodulation field. The preparatory, lower intensity field may be referred to herein as a priming field, as it is used to prime the neural tissue to induce a faster response to the sub-perception neuromodulation field. Thus, priming the neural tissue enables faster pain relief feedback from the patient during the search for the neuromodulation field sweet spot.

While priming neural tissue for purposes of testing sub-perception neuromodulation is specifically discussed as an example, priming neural tissue can be applied to lower the stimulation energy required for both sub-perception neuromodulation and supra-perception neuromodulation, and expedite the response to both test and therapeutic modulations. The energy of the supra-perception neuromodulation delivered to the neuromodulation field is perceptible. The therapeutic neuromodulation is delivered to treat a condition indicated for at least one type of neuromodulation. A test neuromodulation includes neuromodulation delivered for the purposes of testing effectiveness of a therapeutic neuromodulation and/or setting parameters for the therapeutic neuromodulation. For example, a patient suffering from certain types of pain may be indicated for spinal cord neuromodulation as the therapeutic neuromodulation. In similar fashion, a patient suffering from Parkinson's disease (PD), dystonia, essential tremor (ET), or other neurologic disorder of the brain may be indicated for DBS, such as subthalamic nucleus stimulation (STN) or globus pallidus internus (GPi) stimulation. A test neuromodulation may be delivered to find the sweet spot for the neuromodulation field and/or other parameters controlling delivery of the therapeutic neuromodulation, such as pulse waveform, pulse duration, pulse repetition rate, pulse amplitude, and the like. Depending on various factors such as patient preference and effectiveness, sub-perception neuromodulation and/or supra-perception neuromodulation may be delivered as the therapeutic neuromodulation. The target tissue of the neuromodulation can be primed for the test neuromodulation and/or the therapeutic neuromodulation. While specifically discussed for test neuromodulation delivered in preparation for therapeutic sub-perception neuromodulation, various embodiments can include applying the priming techniques (including timing of the priming relative to the therapeutic neuromodulation) discussed in this document to test neuromodulation delivered in preparation for therapeutic sub-perception neuromodulation, test neuromodulation delivered in preparation for therapeutic supra-perception neuromodulation, therapeutic sub-perception neuromodulation, and therapeutic supra-perception neuromodulation.

As some embodiments described herein involve Spinal Cord Stimulation (SC S, also referred to as spinal cord neuromodulation), a brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases.

Some embodiments deliver sub-perception therapy that is therapeutically effective to treat pain, for example, but the patient does not sense the delivery of the neuromodulation field (e.g. paresthesia). Sub-perception therapy may be provided using higher frequency neuromodulation (e.g. about 1500 Hz or above) of the spinal cord. Sub-perception neuromodulation may also be provided through neuromodulation field shaping (e.g., using multiple independent current control, or MICC), and temporal shaping of pulse train (e.g., burst, longer pulses). It appears that these higher frequencies may effectively block the transmission of pain signals in the afferent fibers in the DC. Some embodiments herein selectively modulate DH tissue or DR tissue over DC tissue to provide sub-perception therapy. Such selective neuromodulation may be delivered at lower frequencies. For example, the selective neuromodulation may be delivered at frequencies less than 1,200 Hz. The selective neuromodulation may be delivered at frequencies less than 1,000 Hz in some embodiments. In some embodiments, the selective neuromodulation may be delivered at frequencies less than 500 Hz. In some embodiments, the selective neuromodulation may be delivered at frequencies less than 350 Hz. In some embodiments, the selective neuromodulation may be delivered at frequencies less than 130 Hz. The selective neuromodulation may be delivered at low frequencies (e.g. as low as 2 Hz). The selective neuromodulation may be delivered even without pulses (e.g. 0 Hz) to modulate some neural tissue. By way of example and not limitation, the selective neuromodulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective neuromodulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle.

While SCS is specifically discussed as an example of neuromodulation therapy, various embodiments can also include applying the priming techniques including timing of delivery discussed in this document to Peripheral Nerve Stimulation (PNS) therapies. For example, sub-perception PNS may be applied to alleviate pain. Various embodiments include priming the neural tissue at target locations for delivering the neuromodulation where required intensity of the neuromodulation for testing and/or therapeutic purposes may be lowered.

Figure 2:
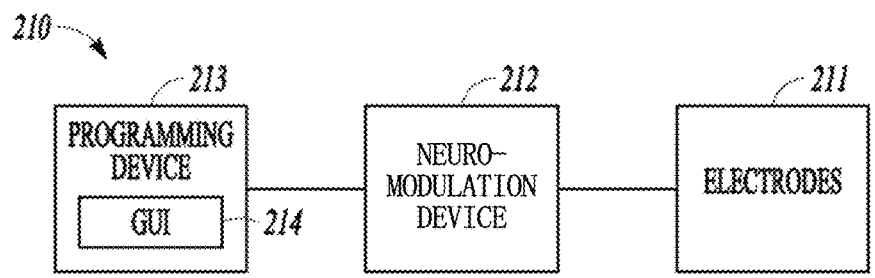
FIG. 2 illustrates, by way of example, an embodiment of a neuromodulation system.

FIG. 2 illustrates an embodiment of a neuromodulation system. The illustrated system 210 includes electrodes 211, a neuromodulation device 212, and a programming device 213. The electrodes 211 are configured to be placed on or near one or more neural targets in a patient. The electrodes 211 may form part of an electrode arrangement. The neuromodulation device 212 is configured to be electrically connected to electrodes 211 and deliver neuromodulation energy, such as in the form of electrical pulses, to the one or more neural targets though electrodes 211. The delivery of the neuromodulation is controlled using a plurality of neuromodulation parameters, such as neuromodulation parameters specifying the electrical pulses and a selection of electrodes through which each of the electrical pulses is delivered. In various embodiments, at least some parameters of the plurality of neuromodulation parameters are programmable by a user, such as a physician or other caregiver. The programming device 213 provides the user with accessibility to the user-programmable parameters. In various embodiments, the programming device 213 is configured to be communicatively coupled to neuromodulation device via a wired or wireless link. In various embodiments, the programming device 213 includes a graphical user interface (GUI) 214 that allows the user to set and/or adjust values of the user-programmable neuromodulation parameters.

In various embodiments, the neuromodulation system 210 can include implantable and external elements. For example, the neuromodulation device 212 can be an implantable neuromodulation device, the electrodes 211 can include electrodes in one or more implantable lead and/or the implantable neuromodulation device, and the programming device can be an external programming device configured to be communicatively coupled to the implantable neuromodulation device via telemetry, as further discussed with reference to FIGS. 5 and 6. In another example, the neuromodulation device 212 can be an external neuromodulation device such as a Transcutaneous Electrical Neural Stimulation (TENS) device, the electrodes 211 can include surface electrodes such as skin patch electrodes, and the programming device can be an external programming device configured to be communicatively coupled to the implantable neuromodulation device via a wired or wireless link, or integrated with the external neuromodulation device. In still another example, the neuromodulation device 212 can be an external neuromodulation device, the electrodes 211 can include percutaneous electrodes, and the programming device can be an external programming device configured to be communicatively coupled to the implantable neuromodulation device via a wired or wireless link, or integrated with the external neuromodulation device. In various embodiments, an external neuromodulation device with surface and/or percutaneous electrodes can be used, for example, for delivering a test neuromodulation, delivering a therapeutic neuromodulation during a trial period, and delivering a short-term therapeutic neuromodulation.

In one embodiment, an external neuromodulation device with surface electrodes can be used during a trial period prior to a potential implantation of an implantable SCS system. A skin patch including the surface electrodes is placed over the patient's spine near the region where percutaneous electrodes will be placed for use during the trial period. The external neuromodulation device such as a dedicated External Trial Stimulator (ETC) and/or an external TENS device is used to prime the neural tissue before the trial period using one or more electrodes selected from the surface electrodes. This allows the programming of the external neuromodulation device for delivering therapeutic neuromodulation through the percutaneous electrodes to be performed with reduced wash-in time, such as immediately following the placement of the percutaneous electrodes.

Figure 3:
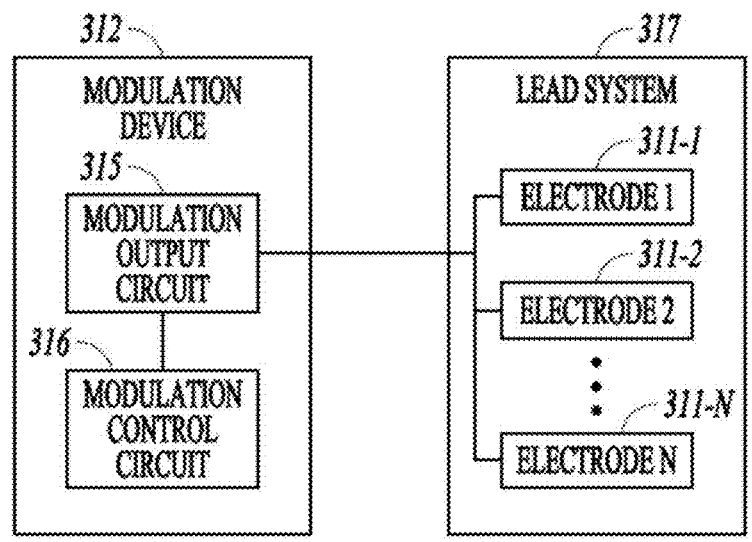
FIG. 3 illustrates, by way of example, an embodiment of a neuromodulation device, such as may be implemented in the neuromodulation system of FIG. 2.

FIG. 3 illustrates an embodiment of a neuromodulation device 312, such as may be implemented in the neuromodulation system 210 of FIG. 2. The illustrated embodiment of the neuromodulation device 312 includes a neuromodulation output circuit 315 and a neuromodulation control circuit 316. Those of ordinary skill in the art will understand that the neuromodulation device 312 may include additional components such as sensing circuitry for patient monitoring and/or feedback control of the therapy, telemetry circuitry and power. The neuromodulation output circuit 315 produces and delivers neuromodulation pulses. The neuromodulation control circuit 316 controls the delivery of the neuromodulation pulses using the plurality of neuromodulation parameters. The combination of the neuromodulation output circuit 315 and neuromodulation control circuit 316 may collectively be referred to as a pulse generator. The lead system 317 includes one or more leads each configured to be electrically connected to neuromodulation device 312 and a plurality of electrodes 311-1 to 311-N (where N≥2) distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between neuromodulation output circuit 315 and tissue of the patient. The neuromodulation pulses are each delivered from the neuromodulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes.

The neuromodulation system may be configured to modulate spinal target tissue, brain tissue, or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "neuromodulation parameter set." Each set of neuromodulation parameters, including fractionalized current distribution to the electrodes (as percentage cathodic current, percentage anodic current, or off), may be stored and combined into a neuromodulation program that can then be used to modulate multiple regions within the patient.

The number of electrodes available combined with the ability to generate a variety of complex electrical pulses, presents a huge selection of neuromodulation parameter sets to the clinician or patient. For example, if the neuromodulation system to be programmed has sixteen electrodes, millions of neuromodulation parameter sets may be available for programming into the neuromodulation system. Furthermore, for example SCS systems may have thirty-two electrodes which exponentially increases the number of neuromodulation parameters sets available for programming. To facilitate such selection, the clinician generally programs the neuromodulation parameters sets through a computerized programming system to allow the optimum neuromodulation parameters to be determined based on patient feedback or other means and to subsequently program the desired neuromodulation parameter sets.

Conventional programming for SCS therapy uses paresthesia to select an appropriate neuromodulation parameter set. The paresthesia induced by the neuromodulation and perceived by the patient should be located in approximately the same place in the patient's body as the pain that is the target of treatment. When leads are implanted within the patient, an operating room (OR) mapping procedure may be performed to apply electrical neuromodulation to test placement of the leads and/or electrodes, thereby assuring that the leads and/or electrodes are implanted in effective locations within the patient. According to various embodiments, programming for sub-perception neuromodulation may prime the neural tissue to provide faster response times to the sub-perception neuromodulation as part of an OR mapping procedure.

Once the leads are correctly positioned, a fitting procedure, which may be referred to as a navigation session, may be performed to program the external control device, and if applicable the neuromodulation device, with a set of neuromodulation parameters that best addresses the painful site. Thus, the navigation session may be used to pinpoint the volume of activation (VOA) or areas correlating to the pain. The procedure may be implemented to target the tissue during implantation, or after implantation should the leads gradually or unexpectedly move that would otherwise relocate the neuromodulation energy away from the target site. By reprogramming the neuromodulation device (typically by independently varying the neuromodulation energy on the electrodes), the VOA can often be moved back to the effective pain site without having to re-operate on the patient in order to reposition the lead and its electrode array. According to various embodiments, a navigation session for sub-perception neuromodulation may prime the neural tissue to provide faster response times to the sub-perception neuromodulation.

Although various embodiments described in this document prime neural tissue to provide faster responses to sub-perception neuromodulation in order to perform faster OR mapping or navigation sessions, the present subject matter is not limited to such programming. By way of example and not limitation, some embodiment may prime the neural tissue before delivering the sub-perception neuromodulation therapy to the neural tissue simply to reduce the wash-in time of the therapy. Thus, by way of example, a patient may obtain pain relief much quicker with the primed neural tissue than without the primed neural tissue.

Figure 4:
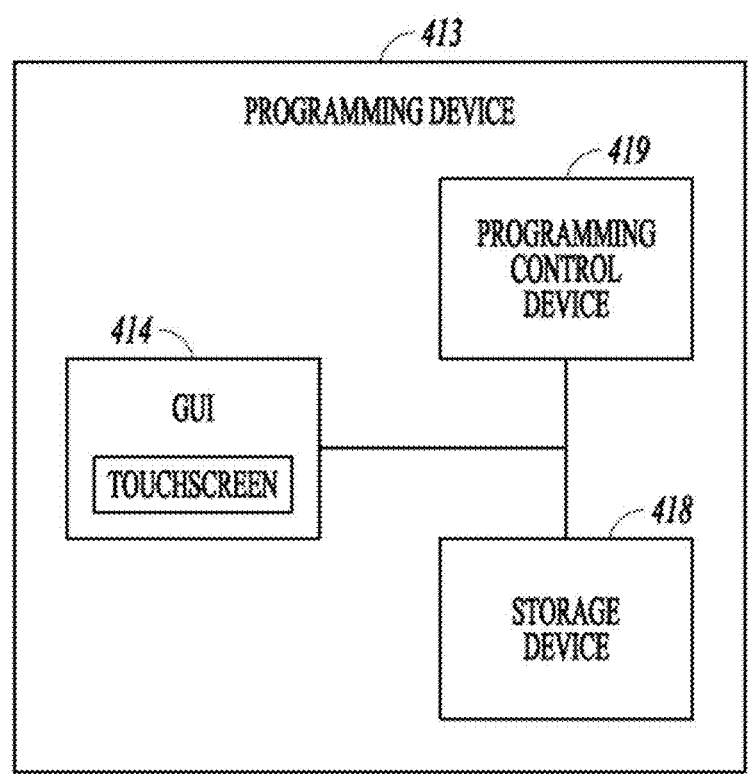
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 418, a programming control circuit 419, and a GUI 414. The programming control circuit 419 generates the plurality of neuromodulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the neuromodulation parameters, such as touchscreen, keyboard, keypad, touchpad, trackball, joystick, and mouse. The storage device 418 may store, among other things, neuromodulation parameters to be programmed into the neuromodulation device. The programming device 413 may transmit the plurality of neuromodulation parameters to the neuromodulation device. In some embodiments, the programming device 413 may transmit power to the neuromodulation device. The programming control circuit 419 may generate the plurality of neuromodulation parameters. In various embodiments, the programming control circuit 419 may check values of the plurality of neuromodulation parameters against safety rules to limit these values within constraints of the safety rules.

In various embodiments, circuits of neuromodulation, including its various embodiments discussed in this document, may be implemented using a combination of hardware, software and firmware. For example, the circuit of a GUI, neuromodulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
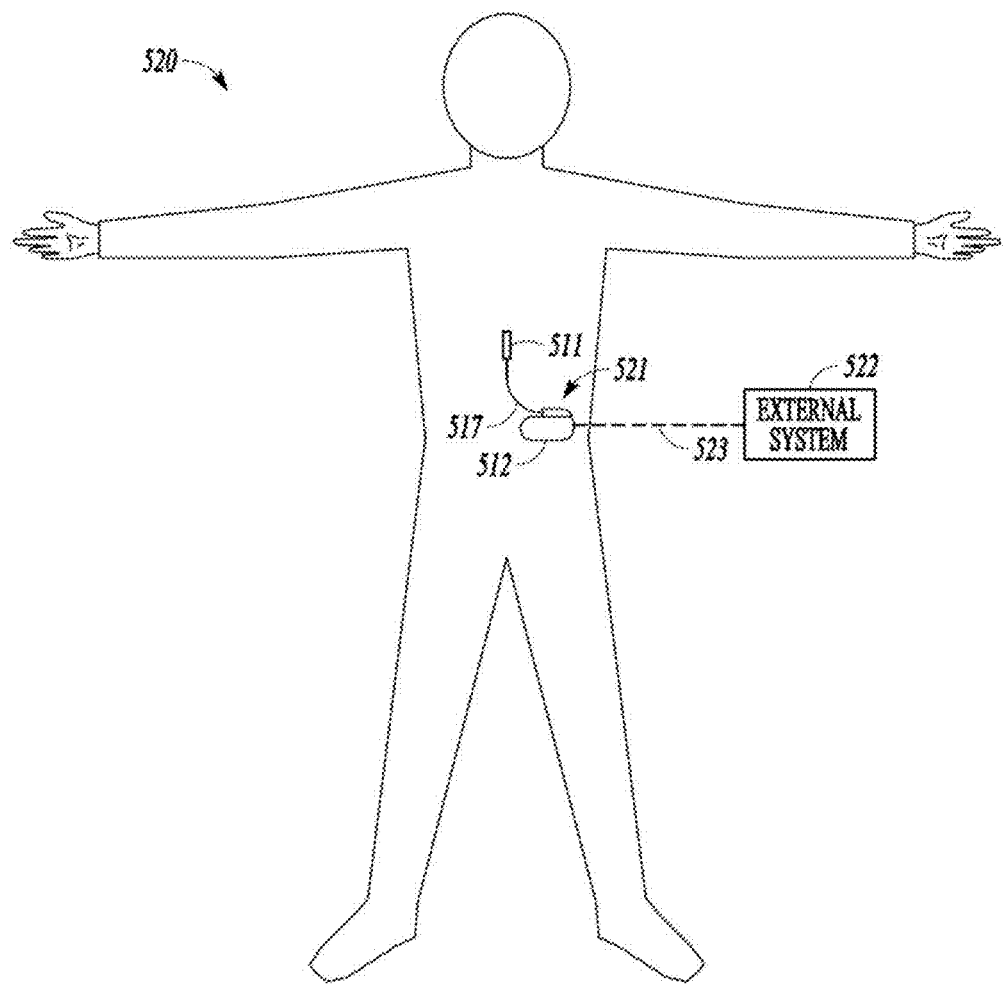
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets such as may be useful for delivering other therapies. The system 520 includes an implantable system 521, an external system 522, and a telemetry link 523 providing for wireless communication between implantable system 521 and external system 522. The implantable system is illustrated as being implanted in the patient's body. The implantable system 521 includes an implantable neuromodulation device (also referred to as an implantable pulse generator, or IPG) 512, a lead system 517, and electrodes 511. The lead system 517 includes one or more leads each configured to be electrically connected to the neuromodulation device 512 and a plurality of electrodes 511 distributed in the one or more leads. In various embodiments, the external system 402 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of neuromodulation parameters.

The neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable neuromodulation device 512 may be implanted in a surgically-made pocket either in the abdomen or above the buttocks, or may be implanted in other locations of the patient's body. The lead extension(s) may be used to facilitate the implantation of the implantable neuromodulation device 512 away from the exit point of the neuromodulation lead(s).

Figure 6:
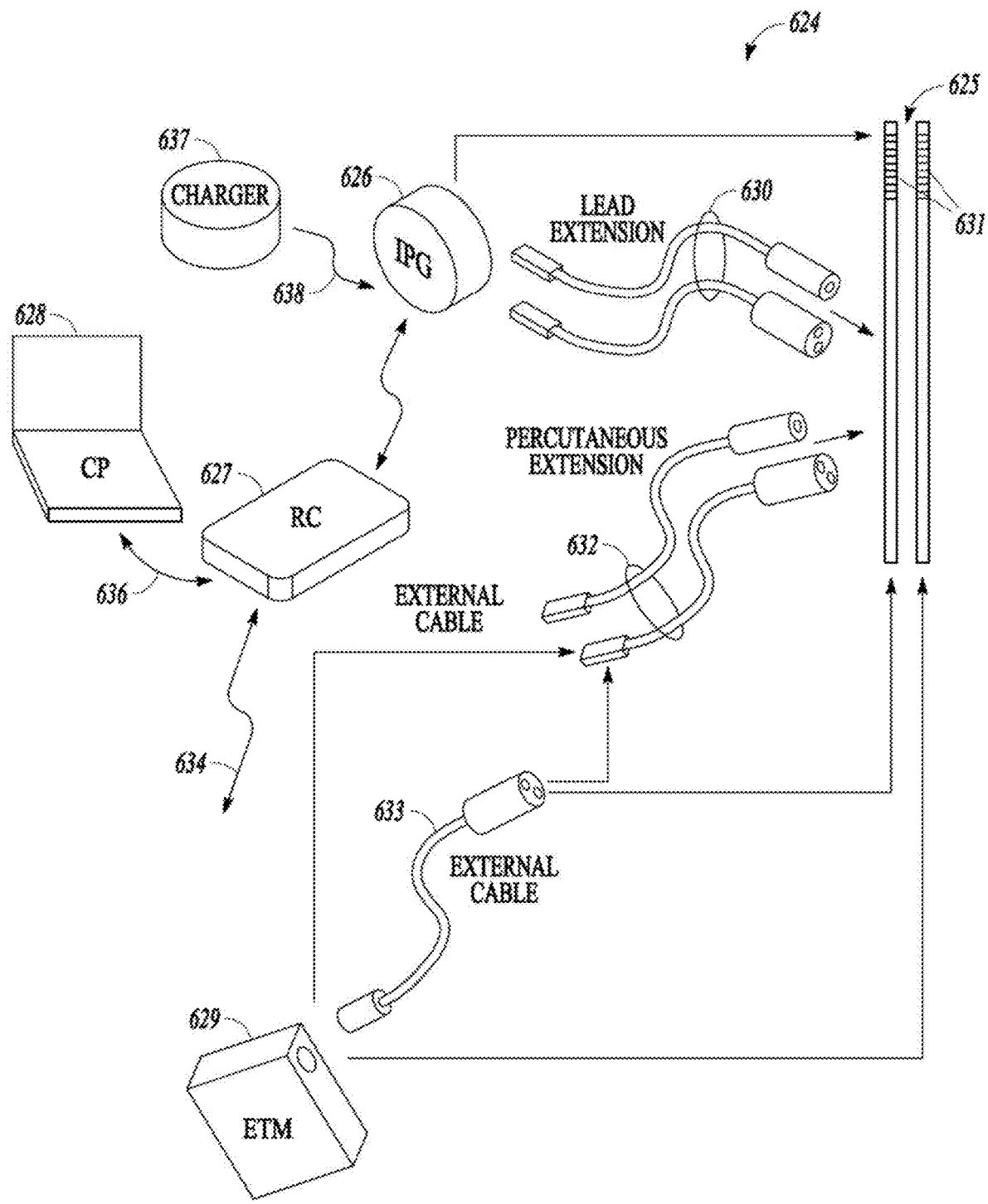
FIG. 6 illustrates, by way of example, an embodiment of a Spinal Cord Stimulation (SCS) system, which also may be referred to as a Spinal Cord Neuromodulation (SCM) system.

FIG. 6 illustrates, by way of example, an embodiment of a SCS system, which also may be referred to as a Spinal Cord Neuromodulation (SCM) system. The SCS system 624 may generally include a plurality (illustrated as two) of implantable neuromodulation leads 625, an implantable pulse generator (IPG) 626, an external remote controller RC 627, a clinician's programmer (CP) 628, and an external trial modulator (ETM) 629. The IPG 626 may be physically connected via one or more percutaneous lead extensions 630 to the neuromodulation leads 625, which carry a plurality of electrodes 631. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 626 includes pulse generation circuitry, also referred to as a pulse generator, that delivers electrical neuromodulation energy in the form of a pulsed electrical waveform (i.e., a temporal series of electrical pulses) to the electrodes in accordance with a set of neuromodulation parameters.

The ETM 629 may also be physically connected via the percutaneous lead extensions 632 and external cable 633 to the neuromodulation leads 625. The ETM 629 may have similar pulse generation circuitry as the IPG 626 to deliver electrical neuromodulation energy to the electrodes accordance with a set of neuromodulation parameters. The ETM 629 is a non-implantable device that is used on a trial basis after the neuromodulation leads 625 have been implanted and prior to implantation of the IPG 626, to test the responsiveness of the neuromodulation that is to be provided. Functions described herein with respect to the IPG 626 can likewise be performed with respect to the ETM 629.

The RC 627 may be used to telemetrically control the ETM 629 via a bi-directional RF communications link 634. The RC 627 may be used to telemetrically control the IPG 626 via a bi-directional RF communications link 635. Such control allows the IPG 626 to be turned on or off and to be programmed with different neuromodulation parameter sets. The IPG 626 may also be operated to modify the programmed neuromodulation parameters to actively control the characteristics of the electrical neuromodulation energy output by the IPG 626. A clinician may use the CP 628 to program neuromodulation parameters into the IPG 626 and ETM 629 in the operating room and in follow-up sessions.

The CP 628 may indirectly communicate with the IPG 626 or ETM 629, through the RC 627, via an IR communications link 636 or other link. The CP 628 may directly communicate with the IPG 626 or ETM 629 via an RF communications link or other link (not shown). The clinician detailed neuromodulation parameters provided by the CP 628 may also be used to program the RC 627, so that the neuromodulation parameters can be subsequently modified by operation of the RC 627 in a stand-alone mode (i.e., without the assistance of the CP 628). Various devices may function as the CP 628. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical neuromodulation generated by the IPG 626 to allow the desired parameters to be determined based on patient feedback or other feedback and for subsequently programming the IPG 626 with the desired neuromodulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical neuromodulation energy output by the neuromodulation leads, and select and program the IPG with neuromodulation parameters in both a surgical setting and a clinical setting.

An external charger 637 may be a portable device used to transcutaneously charge the IPG via a wireless link such as an inductive link 638. Once the IPG has been programmed, and its power source has been charged by the external charger or otherwise replenished, the IPG may function as programmed without the RC or CP being present.

FIG. 7 illustrates, by way of example, some features of the neuromodulation leads 725 and a pulse generator 726. The pulse generator 726 may be an implantable device (IPG) or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable pulse generator (IPG) may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The IPG may include electronic components, such as a controller/processor (e.g., a microcontroller), memory, a battery, telemetry circuitry, monitoring circuitry, neuromodulation output circuitry, and other suitable components known to those skilled in the art. The microcontroller executes a suitable program stored in memory, for directing and controlling the neuromodulation performed by IPG.

Electrical neuromodulation energy is provided to the electrodes in accordance with a set of neuromodulation parameters programmed into the pulse generator. The electrical neuromodulation energy may be in the form of a pulsed electrical waveform. Such neuromodulation parameters may comprise electrode combinations, which define the electrodes that are activated as anodes (positive), cathodes (negative), and turned off (zero), percentage of neuromodulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the neuromodulation on duration X and neuromodulation off duration Y). The electrical pulse parameters may define an intermittent neuromodulation with "on" periods of time where a train of two or more pulses are delivered and "off" periods of time where pulses are not delivered. Electrodes that are selected to transmit or receive electrical energy are referred to herein as "activated," while electrodes that are not selected to transmit or receive electrical energy are referred to herein as "non-activated."

Electrical neuromodulation occurs between or among a plurality of activated electrodes, one of which may be the IPG case. The system may be capable of transmitting neuromodulation energy to the tissue in a monopolar or multipolar (e.g., bipolar, tripolar, etc.) fashion. Monopolar neuromodulation occurs when a selected one of the lead electrodes is activated along with the case of the IPG, so that neuromodulation energy is transmitted between the selected electrode and case.

Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The IPG may be operated in a mode to deliver electrical neuromodulation energy that is therapeutically effective and causes the patient to perceive delivery of the energy (e.g. therapeutically effective to relieve pain with perceived paresthesia, simulated natural-touch sensation, or other supraperception neuromodulation), and may be operated in a sub-perception mode to deliver electrical neuromodulation energy that is therapeutically effective and does not cause the patient to perceive delivery of the energy (e.g. therapeutically effective to relieve pain without perceived paresthesia). Some embodiments may use one channel to prime the neural tissue with a sub-perception neuromodulation field, and use another channel to deliver therapeutic sub-perception neuromodulation to the neural tissue.

The IPG may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

FIG. 8 is a schematic view of a single electrical neuromodulation lead 839 implanted over approximately the longitudinal midline of the patient's spinal cord 840. FIG. 9 illustrates an embodiment where an electrical neuromodulation lead 941 has been implanted more laterally with respect to the spinal cord, thereby placing it proximate the dorsal horn of the spinal cord, and the other electrical neuromodulation lead 942 has been implanted more medially with respect to the spinal cord, thereby placing it proximate the dorsal column of the spinal cord 940.

It is understood that additional leads or lead paddle(s) may be used, such as may be used to provide a wider electrode arrangement and/or to provide the electrodes closer to dorsal horn elements, and that these electrode arrays also may implement fractionalized current.

Placement of the lead more proximate to the DH than the DC may be desirable to preferentially stimulate DH elements over DC neural elements for a sub-perception therapy. Lead placement may also enable preferential neuromodulation of dorsal roots over other neural elements. Any other plurality of leads or a multiple column paddle lead can also be used. Longitudinal component of the electrical field is directed along the y-axis depicted in FIG. 8, and a transverse component of the electrical field is directed along the x-axis depicted in FIG. 8.

FIG. 10 is a schematic view of the electrical neuromodulation lead 1043 showing an example of the fractionalization of the anodic current delivered to the electrodes on the electrical neuromodulation lead. These figures illustrate fractionalization using monopolar neuromodulation where a case electrode of the IPG is the only cathode, and carries 100% of the cathodic current. The fractionalization of the anodic current shown in FIG. 10 does not deliver an equal amount of current to each electrode 1044, because this embodiment takes into account electrode/tissue coupling differences, which are the differences in how the tissue underlying each electrode reacts to electrical neuromodulation. Also, the ends of the portion of the electrical neuromodulation lead include electrodes having lower gradient in the longitudinal direction. The magnitude of the electrical field tapers down at the ends of the electrical neuromodulation lead. Fractionalization of the current may accommodate variation in the tissue underlying those electrodes. The fractionalization across the electrical neuromodulation lead can vary in any manner as long as the total of fractionalized currents equals 100%. Various embodiments described herein implement a programmed algorithm to determine the appropriate fractionalization to achieve a desired neuromodulation field property.

Neuromodulation thresholds vary from patient to patient and from electrode to electrode within a patient. An electrode/tissue coupling calibration of the electrodes may be performed to account for these different neuromodulation thresholds and provide a more accurate fractionalization of the current between electrodes. For example, perception threshold may be used to normalize the electrodes. The RC or the CP may be configured to prompt the patient to actuate a control element, once paresthesia is perceived by the patient. In response to this user input, the RC or the CP may be configured to respond to this user input by storing the neuromodulation signal strength of the electrical pulse train delivered when the control element is actuated. Other sensed parameter or patient-perceived neuromodulation values (e.g. constant paresthesia, or maximum tolerable paresthesia) may be used to provide the electrode/tissue coupling calibration of the electrodes.

The SCS system may be configured to deliver different electrical fields to achieve a temporal summation of neuromodulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle.

Some embodiments are configured to determine a neuromodulation parameter set to create a field shape to provide a broad and uniform neuromodulation field such as may be useful to prime targeted neural tissue with sub-perception neuromodulation. Some embodiments are configured to determine a neuromodulation parameter set to create a field shape to reduce or minimize neuromodulation of non-targeted tissue (e.g. DC tissue). The neuromodulation field may be shaped by using multiple independent current control (MICC) or multiple independent voltage control to guide the estimate of current fractionalization among multiple electrodes and estimate a total amplitude that provide a desired strength. For example, the neuromodulation field may be shaped to enhance the neuromodulation of DH neural tissue and to minimize the neuromodulation of DC tissue. A benefit of MICC is that MICC accounts for various in electrode-tissue coupling efficiency and perception threshold at each individual contact, so that "hot-spot" stimulation is eliminated.

Sub-perception SCS typically does not provide a quick feedback response regarding the effectiveness of the therapy. Rather, it has been observed that a wash-in period (a period of time for a delivered therapy to be therapeutically effective) for the sub-perception SCS is typically about one day. Thus, when the programmed neuromodulation parameters are changed to change the location of the sub-perception neuromodulation field, the patient may not be able to determine the effect that the changes have (e.g. pain relief) for a day or so. This make it difficult quickly titrate the neuromodulation field of the sub-perception SCS to provide effective pain relief to the patient.

It has been observed during research that priming the neural tissue enables faster pain relief feedback from the patient during the search for the neuromodulation field sweet spot. It may be appropriate to consider that priming the neural tissue "warms up" the neural tissue in a manner that reduces the wash-in time. However, neural physiology is complex and it is not currently understood why the primed neural tissue reduces the wash-in time of the sub-perception therapy such that the patient can quickly feel pain relief. It is noted that "priming" is different than conditioning pre-pulses which are delivered immediately before the neuromodulation pulse. A conditioning pre-pulse is timed to make a nerve more susceptible or less susceptible to capture by the immediately subsequent neuromodulation pulse. Thus, a conditioning pre-pulse has a specific relationship to a neuromodulation pulse. In contrast, the prime neuromodulation field extends over a much longer period of time. Further, rather than making neural tissue more or less excitable by a pulse, the prime neuromodulation field reduces a wash-in time of a therapy to make a patient feel the effects of the therapy (e.g. pain relief) much more quickly than would be felt without the prime field.

Various embodiments may deliver a low intensity, neuromodulation field in preparation to test for and find the sweet-spot for the neuromodulation field. The preparatory, lower intensity field is referred to herein as a prime field, as it is used to prime the neural tissue to be tested to have a quicker response to during the testing for the neuromodulation sweet spot for pain relief. The prime field can be a supra-perception or sub-perception neuromodulation field, but is typically even lower than the therapeutic sub-perception neuromodulation field.

A test region of neural tissue represents a region of tissue that is to be tested for a sweet spot. The test region may include many potential locations for targeting the neuromodulation field. The test region may span along the entire electrode arrangement (e.g. lead(s)) or may be reduced to a portion of the electrode arrangement. Priming may also be applied in a trolling fashion to cover the entire test region. As it is not known what location is to be most effective, the entire test region is primed.

In a non-limiting example to illustrate the lower intensity of the prime neuromodulation field, one may assume that a patient may feel paresthesia or otherwise perceive the delivery of the neuromodulation field when the neuromodulation current has an amplitude of 10 mA. Thus, 10 mA may be considered to be a perception threshold for the neuromodulation. Therapeutic sub-perception neuromodulation maybe delivered within a range of 30% to 90% of the perception threshold. Thus, in this example, neuromodulation with an amplitude between 3 mA and 9 mA may be therapeutically effective (e.g. provide pain relief). Priming the neural tissue may be accomplished using amplitudes near the lower range of the sub-perception neuromodulation or even below the lower range of the sub-perception neuromodulation such as, by way of example, between 2 mA to 4 mA. The sub-perception neuromodulation affects the neural tissue, but not to the point where the neuromodulation induces the nerve to trigger action potentials. Thus, the prime field may affect the ion concentrations within and outside of the neural pathways responsible for pain relief and/or may affect neurotransmitters responsible for pain relief, such that additional changes by sub-perception neuromodulation may more quickly induce desirable action potentials in these neural pathways responsible for pain relief.

FIGS. 11A-11B illustrate, by way of example and not limitation, electrode arrangements (e.g. E1-E8 in FIG. 11A and E1-E16 in FIG. 11B) and test regions 1145 of neural tissue along the electrode arrangements. These test regions 1145 may extend across the entire electrode arrangement. In some embodiments, the test regions may extend along only a portion of the electrode arrangement. By way of example, some embodiments may allow a user to select the test region and thus select the portion of the electrode arrangement to be tested. In the example illustrated in FIG. 11A the test region is neural tissue along the E2 to E7 electrodes, and in the example illustrated in FIG. 11B the test region is neural tissue along the E2 through E7 and the E10 to E15 electrodes.

The electrodes in the electrode arrangement may be fractionalized, using different neuromodulation parameter sets, to change the portion of the neural tissue that is modulated. Thus, there may be many neural tissue locations that can be targeted with the test region of neural tissue adjacent to the electrode arrangement. FIGS. 12A-12C illustrate, by way of example and not limitation, neural tissue locations 1246 that may be targeted within the test region in one, two and three dimensions, respectively. In the one-dimensional example illustrated in FIG. 12A, the neural locations that may be targeted may simply be a line of potential targets such as may be observed from a single lead with a linear arrangement of electrodes. In the two dimensional example illustrated in FIG. 12B the neural locations that may be targeted may be considered to lie in a plane proximate to the electrode arrangement. In the three-dimensional example illustrated in FIG. 12C, the neural locations that may be targeted may be considered to be a volume of tissue proximate to the electrode arrangement. By way of example, the two-dimensional and three-dimensional test regions may be implemented using two or more leads of electrodes. Thus, the test regions may be relatively simple or complex shapes, and may include relatively few or relatively many locations to be tested.

Figure 13:
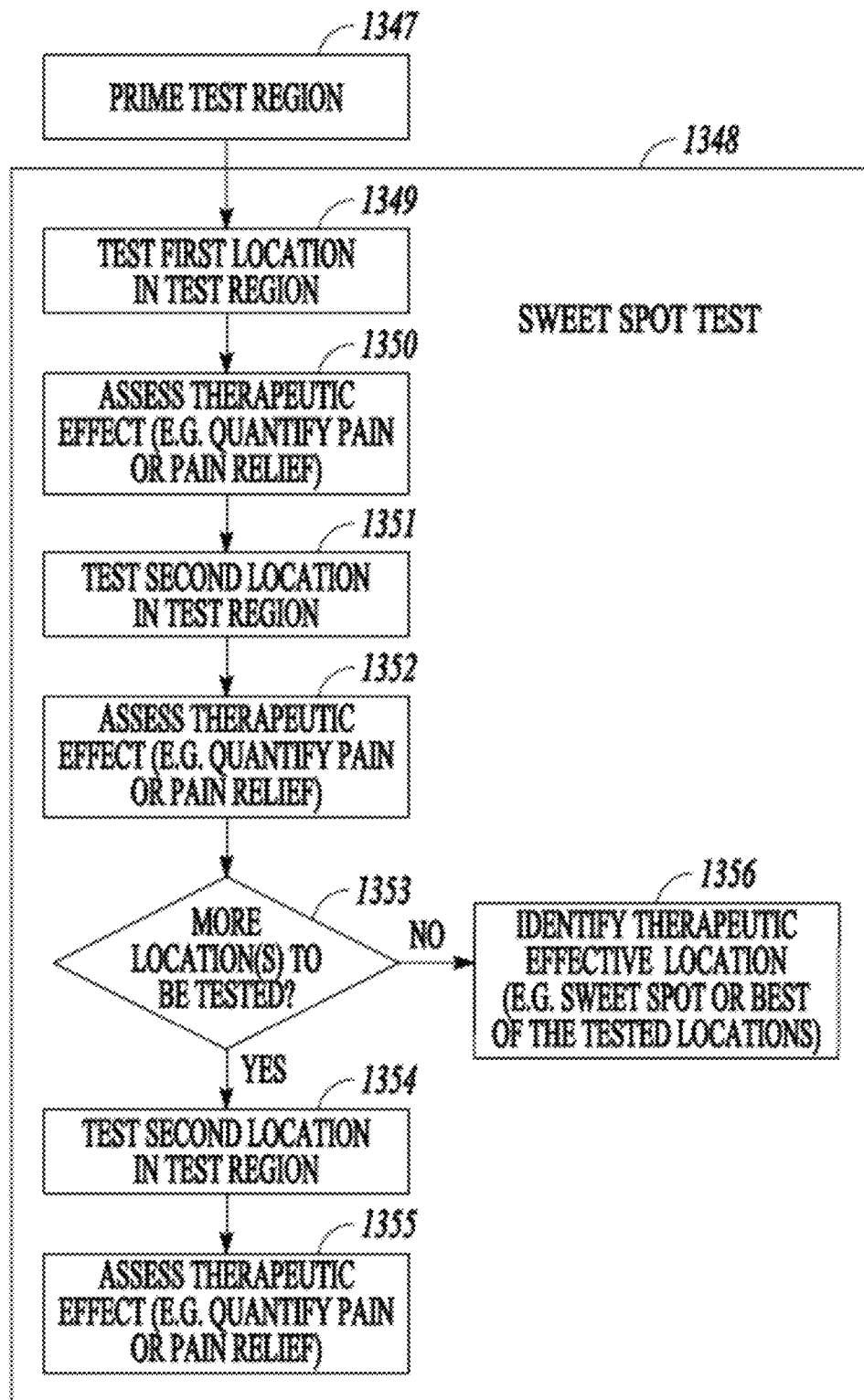
FIG. 13 illustrates an example of a method for finding a sweet spot for sub-perception neuromodulation.

FIG. 13 illustrates an example of a method for finding a sweet spot for sub-perception neuromodulation. In the illustrated example, a test region is primed with the sub-perception neuromodulation field 1347, and the sweet-spot test is performed 1348 to find location of neural tissue that is therapeutically effective when targeted with sub-perception neuromodulation. The sweet spot test may involve a manual process to reprogram the neuromodulation field parameter set with different values to change the targeted location of the neuromodulation field. In some embodiments of the test, the targeted location is automatically changed (e.g. trolled) by automatically changing values of the neuromodulation field parameter set. Some embodiments may semi-automatically change values of the neuromodulation field parameter set to change the targeted location of the neuromodulation field.

At 1349, a first location in the test region is tested by focusing the neuromodulation field onto the first location. At 1350, the therapeutic effect of modulating the first location is assessed. In an example where the therapy is a therapy to alleviate pain, the patient may provide this assessment by quantifying a level of pain or level of pain relief that they are experiencing. In some examples, a biomarker is used to provide an assessment of the therapeutic efficacy of the neuromodulation field focused on the tested location. At 1351, the neuromodulation field parameter set is changed to change the focus of the neuromodulation field to test a second location in the test region. At 1352, the therapeutic effect of modulating the second location is assessed. If more location(s) are to be tested, as illustrated at 1353, the process may continue to 1354 to test the next location and to 1355 to assess the therapeutic effect of the next location. The process may determine or identify the location(s) that are therapeutically effective 1356 by evaluating the quantified effects of the therapy. In some embodiments, the quantified effects may be compared to each other to identify the tested location that has the best therapeutic effect (the sweet spot) or one of the best therapeutic effects (a sweet spot).

The present subject matter may be used to test relatively small locations using a more narrowly focused neuromodulation field such as generally illustrated above in FIGS. 12A-12C, or may be used to test relatively larger locations of neural tissue using a more uniform (less focused) neuromodulation field. The test of larger locations may be followed by a more focused test or tests within one of the larger location. Regardless of whether the test location is relatively large or relatively small, the present subject matter primes the test neural tissue to reduce a wash-in time of the therapy and enable a quick assessment of the effectiveness of the therapy. A few search algorithms are provided below as examples. Other processes for testing locations of neural tissue are possible.

Various embodiments start with full-lead then use a search algorithm to reduce the span and improve energy efficiency. This can be done from the RC or CP, or in the IPG with RC feedback. The proposed algorithms may rely on some form of feedback indicating the effectiveness of the neuromodulation. For example, a patient may provide feedback regarding pain relief. Feedback may also provide a biomarker signal.

The system may include a routine to confirm that the neuromodulation along the full lead is effective and then focus the neuromodulation along a portion of the lead. Thus, for example, a generally uniform neuromodulation field may be provided along this smaller portion of the lead. This field is still broad as it may be provided across an area with multiple electrode contacts, but it is less than the entire electrode arrangement using electrode array(s) on the lead(s).

Various embodiments may provide a rostra-caudal focus routine that includes a binary search routine. The binary search routine segments the lead or array of electrodes from a full set of electrodes into at least two subsets of electrodes that defines partial lead search regions. The binary search routine may confirm that neuromodulation along the full lead is effective.

Figure 14:
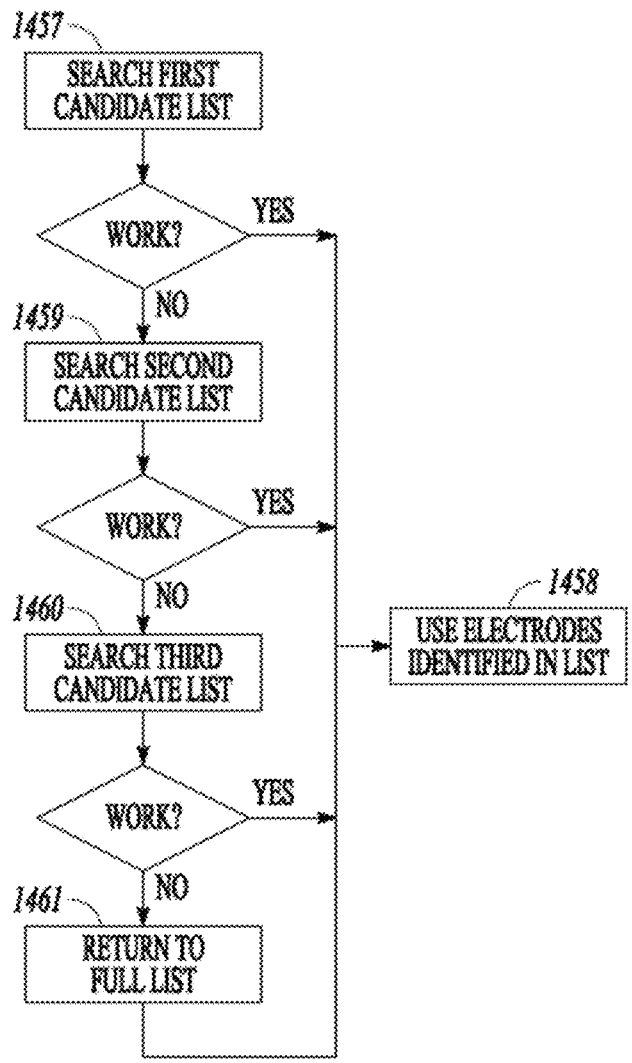
FIG. 14 illustrates, by way of example, aspects of a binary search routine as a rostra-caudal focus routine.

FIG. 14 illustrates, by way of example, aspects of a binary search routine as a rostra-caudal focus routine. A first subset of electrodes that define a first partial lead search region can be tested to determine if the neuromodulation is effective using the first subset 1457. If it is effective, the first subset of electrodes that define the first partial lead search region may be used to deliver the neuromodulation 1458 or for further more focused tests. If it is not effective, then a second subset of electrodes that define a second partial lead search region may be tested to determine if the second subset of electrodes is effective 1459. If it is effective, the second subset of electrodes that define the second partial lead search region may be used to deliver the neuromodulation 1458. If it is not effective, then a third (or nth) subset of electrodes that define a third (or nth) partial lead search region may be tested to determine if the third (or nth) subset of electrodes is effective 1460. If it is effective, the third (or nth) subset of electrodes that define the third (or nth) partial lead search region may be used to deliver the neuromodulation 1458. If it is not effective, then the binary search process may return to the full list of electrodes 1461 which was previously determined to be effective. At least some of the subsets of electrodes may be exclusive of each other. At least some of the subsets of electrodes may intersect with each other. In some embodiments, at least two subsets are exclusive, and at least one subset has an intersection with another subset.

Figure 15:
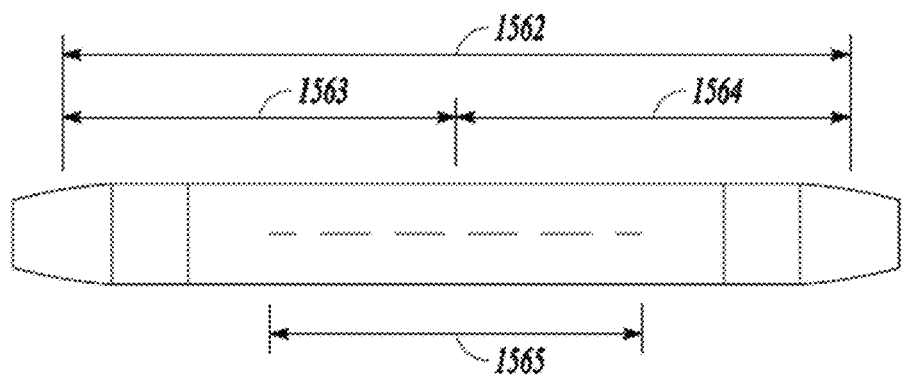
FIG. 15 illustrates an example of the binary search routine.

FIG. 15 illustrates an example of the binary search routine. The lead has a full span 1562 which may be split into three partial lead search regions 1563, 1564 and 1565, each partial search region including a corresponding subset of electrodes. By way of example and not limitation, the first and second subsets 1563 and 1564 of electrodes may be mutually exclusive, and third subset 1565 may include an intersection with the first subset and also may include an intersection with the second set. In an example, the full lead may be bifurcated to provide the first partial lead search region 1563 on a first side of the lead (e.g. left end of electrode array to middle) and the second partial lead search region 1564 on a second side of the lead (e.g. right end of the electrode array to middle). The third partial lead search region 1565 may partially overlap each of the first and second partial lead search regions. Thus, the partial lead search regions may define a first end region, a second end region and a middle region of the lead.

Figure 16A:
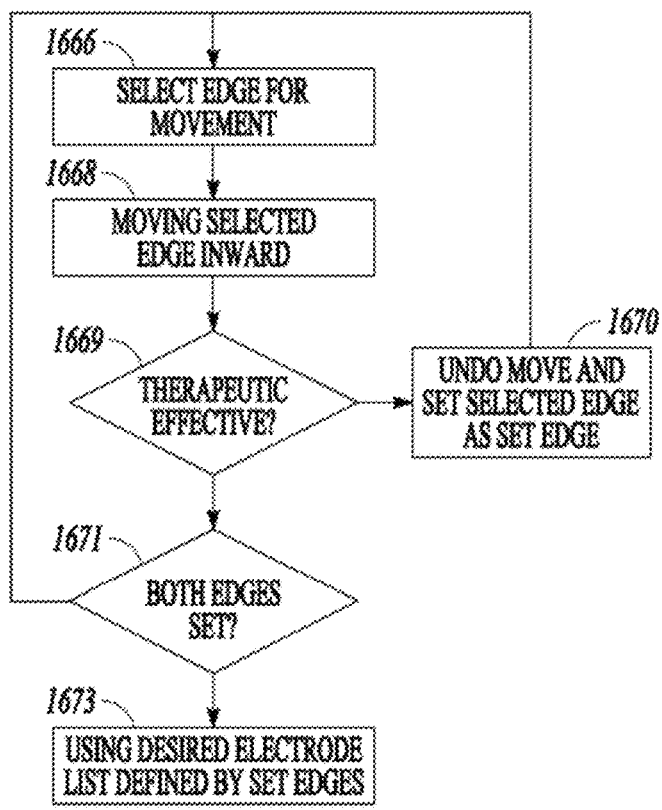
FIGS. 16A-16C illustrate, by way of example, an edge search routine.
Figure 16B:
Figure 16C:
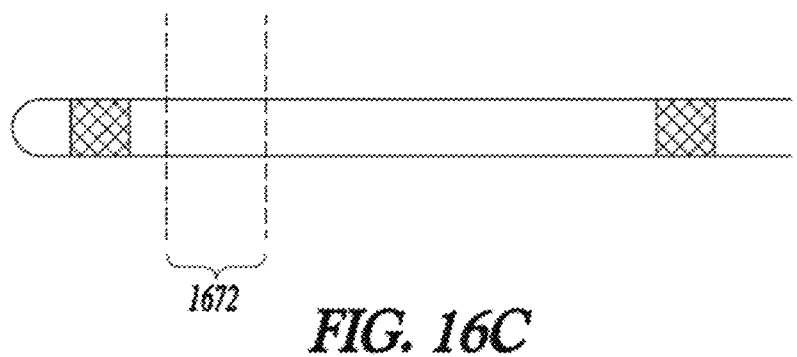

FIGS. 16A-16C illustrate, by way of example, an edge search routine. The edge search routine progressively moves each edge of the active electrodes in the array toward the middle and confirms that the neuromodulation remains effective with the moves. Thus, a first edge can be moved toward the center until the next move toward the center causes the neuromodulation to be ineffective; and a second edge can be moved toward the center until the next move toward the center causes the neuromodulation to be ineffective.

For example, the edge search routine may include selecting an edge of the electrode arrangement (e.g. array) for movement 1666. The selected edge may be one of the two edges 1667A or 1667B illustrated in FIG. 16B. However, there can be more than two edges if more than two regions are being focused. The selected edge is moved inward 1668 toward the other edge for the region of interest. If the reduced set of electrodes is no longer therapeutically effective 1669, then the previous move can be undone and that edge can be set so that is no longer is capable of being selected for movement 1670. The process can return to 1666 to attempt to move the other edge(s). If the reduced set of electrodes continues to be therapeutically effective 1669, then the process returns to 1666 to continue moving edges until such time as all of the edges are set 1671. The final reduced set 1672 of electrodes can be used 1673 to deliver the neuromodulation energy.

According to various embodiments, the programmed system may be configured with a neuromodulation focus routine such as a rostra-caudal focus routine to allow a user to select the desired electrodes for the neuromodulation to be more specific to the desired physiological area. Some embodiments may allow non-contiguous spans to be selected as a result of initial programming and/or neuromodulation refinement later on.

The neuromodulation field may be moved from location to location using an automatic trolling process or through patient control. Candidate trolling algorithms include a monopolar troll (anodic or cathodic) or a bipolar troll or a multipolar troll. The troll can be done with MICC or multiple independent voltage control, or with a timing channel interleaving technique. MICC enables the locus of the neuromodulation to be gradually moved across along the lead or within the array of electrodes. The interleaving of timing channels allows different electrode(s) in different timing channels. Values of stimulation parameter(s) (e.g. amplitude) in the timing channels can be adjusted. Thus by way of example and not limitation, if a monopolar neuromodulation is delivered using a first electrode in a first channel and another monopolar neuromodulation is delivered using a second electrode adjacent to the first electrode in a second channel, then the amplitude of the monopolar neuromodulation in the first channel may be incrementally reduced as the amplitude of the monopolar neuromodulation may be increase in the second channel. In this matter, the locus of the neuromodulation may be gradually adjusted.

Various embodiments troll a neuromodulation field, using an arrangement of electrodes on at least one lead, through neural tissue positions, and perform a quantification procedure multiple times as the neuromodulation field is trolled through the positions. The quantification procedure identifies when the neuromodulation field provides a therapeutic effect (e.g. pain relief). The quantification procedure may include receiving a marking signal that indicates that a neuromodulation intensity achieved the therapeutic effect, and storing a value for the therapeutic effect as well as neuromodulation field parameter data. The neuromodulation intensity may include neuromodulation parameters that affect the patient's perception of the neuromodulation energy. These parameters may include pulse width, rate, amplitude, distribution of current, and electrode polarity (cathode v. anode). By way of example and not limitation, the storage of the parameter data may be in a temporary storage such as but not limited to cache or RAM or in permanent/persistent storage such as but not limited to ROM, a memory device such a hard drive, optical disc, thumb drive, or cloud storage. The quantification process may include receiving a titration signal that indicates an instruction to adjust neuromodulation intensity, and adjusting the neuromodulation intensity in response to receiving the titration signal. The titration signal may be initiated by a patient, or by a clinician or other user who is responding to patient responses.

Figure 17:
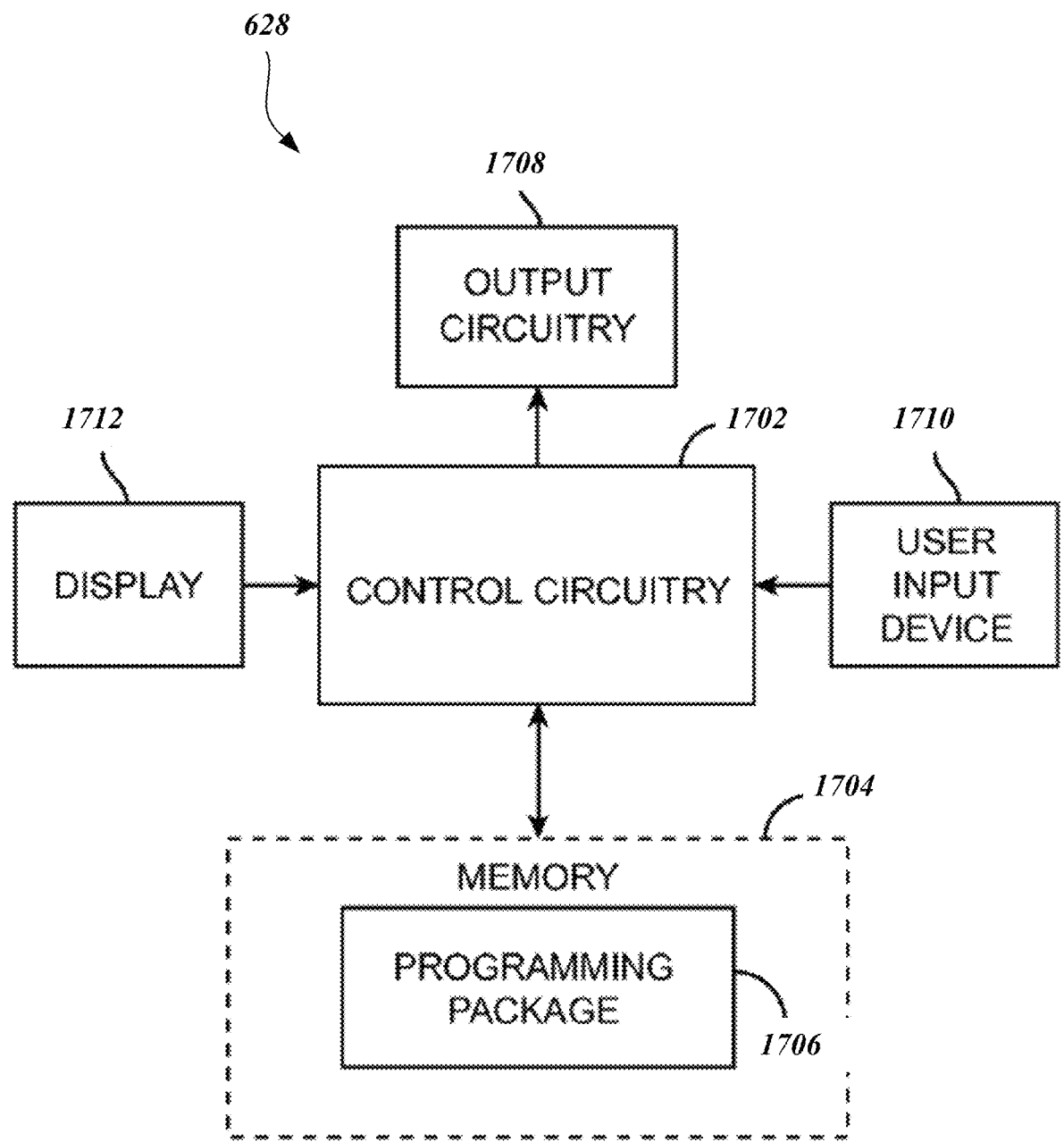
FIG. 17 is a diagram illustrating a programming device in greater detail according to an embodiment.

FIG. 17, is a diagram illustrating the CP 628 (FIG. 6) in greater detail. CP 628 includes a control circuitry 1702 (e.g., a central processor unit (CPU)) and memory 1704 that stores a stimulation programming package 1706, which can be executed by the control circuitry 1702 to allow the user to program the IPG 626 (FIG. 6), and RC 627 (FIG. 6). The CP 628 further includes output circuitry 1708 (e.g., via the telemetry circuitry of the RC 627) for downloading stimulation parameters to the IPG 626 and RC 627 and for uploading stimulation parameters already stored in the memory of the RC 627, via the telemetry circuitry of the RC 627.

Execution of the programming package 1706 by the control circuitry 1702 provides a multitude of display screens shown on display 1712 that can be navigated through via use of user input device 1710. These display screens allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads, and select and program the IPG 626 with stimulation parameters in both a surgical setting and a clinical setting.

In various embodiments, execution of the programming package 1706 provides a user interface that conveniently allows a user to program the IPG 626 to produce a user-customized stimulation field, which may include the placement and movement of customized target poles. In various examples, the programming package 1706, when executed by control circuitry 1702, implements a set of engines for facilitating the user interface in which fields or target poles may be defined, mapping the field or target pole definitions to physical electrodes and electrical energy application parameters for establishing the defined fields and target poles, supervising the establishment and variation of the fields and target poles to comply with safety and other defined constraints, and optimizing the energy utilization in the operation of the IPG 626.

In the examples described above, and in various other embodiments, the components described herein are implemented as engines, circuits, components, modules, or other structures, which for the sake of consistency are termed engines, although it will be understood that these terms may be used interchangeably. Engines may be hardware, software, or firmware communicatively coupled to one or more processors in order to carry out the operations described herein. Engines may be hardware engines, and as such engines may be considered tangible entities capable of performing specified operations and may be configured or arranged in a certain manner. In an example, circuits may be arranged (e.g., internally or with respect to external entities such as other circuits) in a specified manner as an engine. In an example, the whole or part of one or more hardware processors may be configured by firmware or software (e.g., instructions, an application portion, or an application) as an engine that operates to perform specified operations. In an example, the software may reside on a machine-readable medium. In an example, the software, when executed by the underlying hardware of the engine, causes the hardware to perform the specified operations. Accordingly, the term hardware engine is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein.

Considering examples in which engines are temporarily configured, each of the engines need not be instantiated at any one moment in time. For example, where the engines comprise a general-purpose hardware processor core configured using software; the general-purpose hardware processor core may be configured as respective different engines at different times. Software may accordingly configure a hardware processor core, for example, to constitute a particular engine at one instance of time and to constitute a different engine at a different instance of time.

One aspect of the embodiments is directed to configuring a neuromodulation device such as neuromodulation device 212 (FIG. 2) or IPG 626 (FIG. 6). According to some embodiments, which are described in greater detail below, a neuromodulation system such as system 210 (FIG. 2) or the SCS system of FIG. 6, facilitates anatomy-based targeting control of the neuromodulation.

Figure 18:
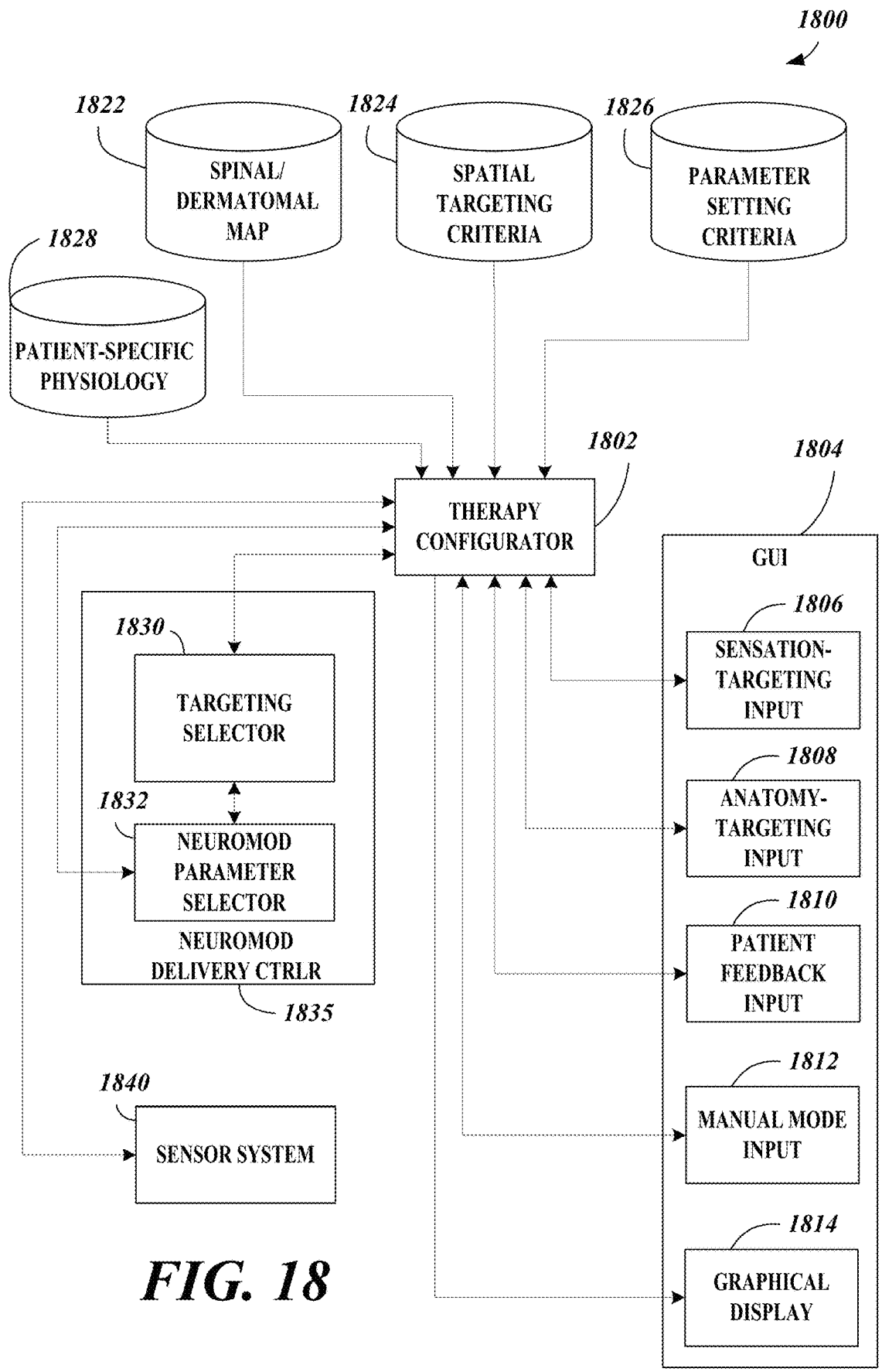
FIG. 18 is a diagram illustrating the structure and operation of an example anatomic-based controller for a neuromodulation device, according to some embodiments.

FIG. 18 is a diagram illustrating the structure and operation of an example anatomic-based controller 1800 for a neuromodulation device, according to some embodiments. Therapy configurator 1802 is constructed, programmed, or otherwise configured, to interpret user input, and to present operational and configuration information for the neuromodulation device, to the user via GUI 1804. In addition, therapy configurator 1802 interfaces with databases 1822-1828, the contents of which are described below, and passes relevant information between these databases and GUI 1804. In addition, therapy configurator 1802 passes commands from GUI 1804 to neuromodulation delivery controller 1835, which includes targeting selector 1830 and neuromodulation parameter selector 1832. Furthermore, in a related embodiment, therapy configurator 1802 passes information obtained by sensor system 1840 to neuromodulation delivery controller 1835.

In the embodiment depicted, GUI 1804 facilitates sensation-targeting input 1806, anatomy-targeting input 1808, patient feedback input 1810, and manual mode input 1812. Also, GUI 1804 facilitates graphical display 1814 to be displayed on a monitor, touchscreen, or other suitable output device.

Figure 19A:
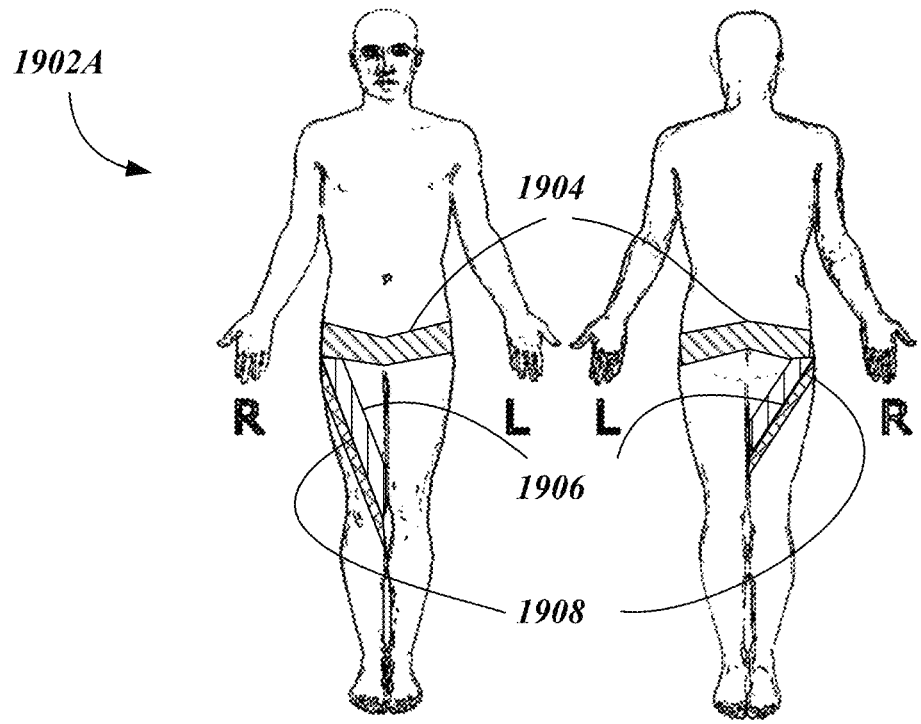
FIGS. 19A-19C are diagrams illustrating interactive graphical user interface (GUI) elements facilitating neuromodulation control input according to various embodiments.
Figure 19B:
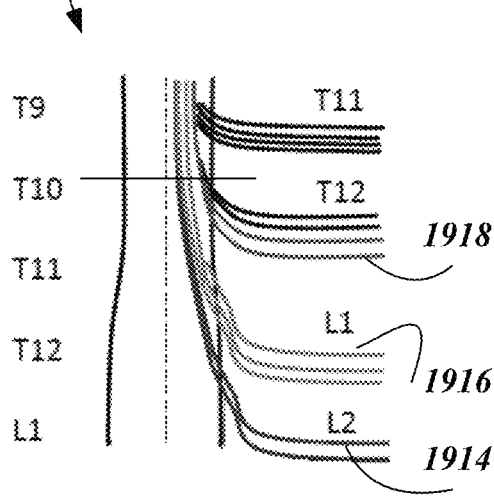
Figure 19C:
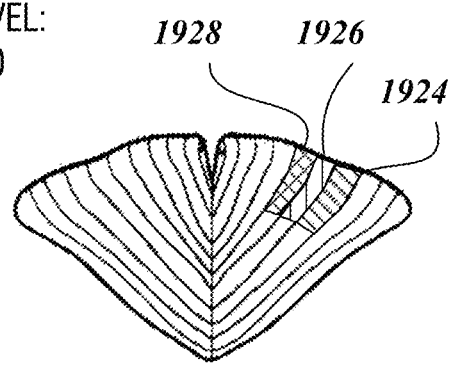

FIGS. 19A-19C are diagrams of interactive GUI elements 1902A-1902C facilitating neuromodulation control input according to various embodiments. FIG. 19A illustrates an interactive graphical input engine that realizes sensation-targeting input 1806 and anatomy-targeting input 1808 (FIG. 18), as well as graphical display 1814, which displays anterior and posterior anatomical views of a human form. Notably, in the embodiment depicted, the front and back anatomical views contain active elements that may be activated by user input. For instance, in the example depicted, the user may select regions of the body where the patient reports pain. Selection may be accomplished according to various embodiments by clicking on points in the display, placing a cursor or pointer at certain points, using a dragged selector box or a free-form selector boundary, etc.

In a related embodiment, neuroanatomical data, such as the locations of dermatomes, and their association with dorsal roots, dorsal columns, and tracts of nerve fibers extending peripherally from the dorsal roots, is incorporated in the interactive graphical input engine. In a related embodiment, user-interaction with the sensation-targeting input 1806, such as indication of pain location, causes the sensation-targeting input 1806 to automatically highlight portions of the anatomic display corresponding to the organization of the nervous system. For instance, as depicted in FIG. 19A, in response to the patient reporting lower-back pain, region 1904, representing the dermatome corresponding to the reported area of back pain, are illuminated. Similarly, regions 1906 and 1908, corresponding to dermatomes on the right leg where pain was reported by the patient, are illuminated when selected for treatment.

In a related embodiment, the anatomical data is mapped to neuromodulation treatment locations, also referred to herein as target regions for neuromodulation. These target regions may be in a similar, or different, location from the location where the patient reports pain sensation. FIG. 19B is a posterior-view diagram illustrating the dorsal column including some of the dorsal roots. FIG. 19C is a diagram illustrating a pertinent section, (T10 in this case) of the dorsal column shown in FIG. 19B. Highlighted dorsal roots 1914 correspond to highlighted dermatome 1904; highlighted dorsal roots 1916 correspond to highlighted dermatome 1906, and highlighted dorsal roots 1918 correspond to highlighted dermatome 908. These dorsal roots are highlighted in response to user selection of pain sites based on the neuroanatomical data.

Similarly, in FIG. 19C, sections of the dorsal column 1924, 1926, and 1928 are highlighted in response to the user selection of pain sites based on the neuroanatomical data. The highlighted dorsal roots or dorsal column portions may accordingly be targeted for neuromodulation therapy.

In a related embodiment, GUI active elements of FIGS. 19B and 19C may also be used to control the selection of neuromodulation targeting. For instance, a user may select dorsal root fibers 1914, 1916, or 1918 among the lumbar or thoracic nerves, for instance. In this case, the system may treat the selection of nerve fibers as indications of the nerve fibers associated with the patient's reported pain. In another embodiment, where those nerve fibers are themselves subject to neuromodulation therapy, selection of nerve fibers may be treated by the system as a user command to target the nerve fibers as the neuromodulation target regions. In this particular example, active elements 1902B may implement anatomy-targeting input 1808.

Similarly, a user may select portions of the dorsal column, such as portions 1924-1928. The system may treat these dorsal column portions as those associated with the pain, or as neuromodulation target regions in embodiments where neuromodulation is configured for dorsal root targeting. In this particular example, active elements 1902C may also implement anatomy-targeting input 1808.

Referring again to FIG. 18, in a related embodiment, therapy configurator 1802 passes the pain-location data to neuromodulation delivery controller 1835. Targeting selector 1830 is programmed, or otherwise configured, to use the pain-location data and corresponding neuroanatomical information from which the corresponding neuromodulation site(s) may be determined, to computationally determine an electrode configuration, which includes electrode current fractionalization and establishment of virtual electrodes, that directs a neuromodulation field to target regions in the patient. The target regions may include dorsal column regions, dorsal root regions, dorsal horn regions, and other regions that may produce a beneficial clinical effect such as suppression of pain, with paresthesia, or without paresthesia. In a related embodiment, neuromodulation parameter selector 1832 is programmed, or otherwise configured, to determine electrical parameters, including electric field levels and waveforms, for neuromodulation to be applied to each target region. Various neuromodulation parameters may be optimized for the target region based on the type or size of neural tissue, for example. Also, user preferences or user-specifications may be taken into account for determining the neuromodulation parameters. For instance, in an example embodiment, the user may specify, or indicate a preference for, paresthesia or non-paresthesia via GUI 1804. In a related embodiment, the user may specify an exclusion zone where there should be no neuromodulation, or no modulation of a specified type (e.g., perceptible neuromodulation, sub-perception neuromodulation, etc.) applied. Operation of targeting selector 1830 and neuromodulation parameter selector 1832 is described in greater detail below.

Figure 20A:
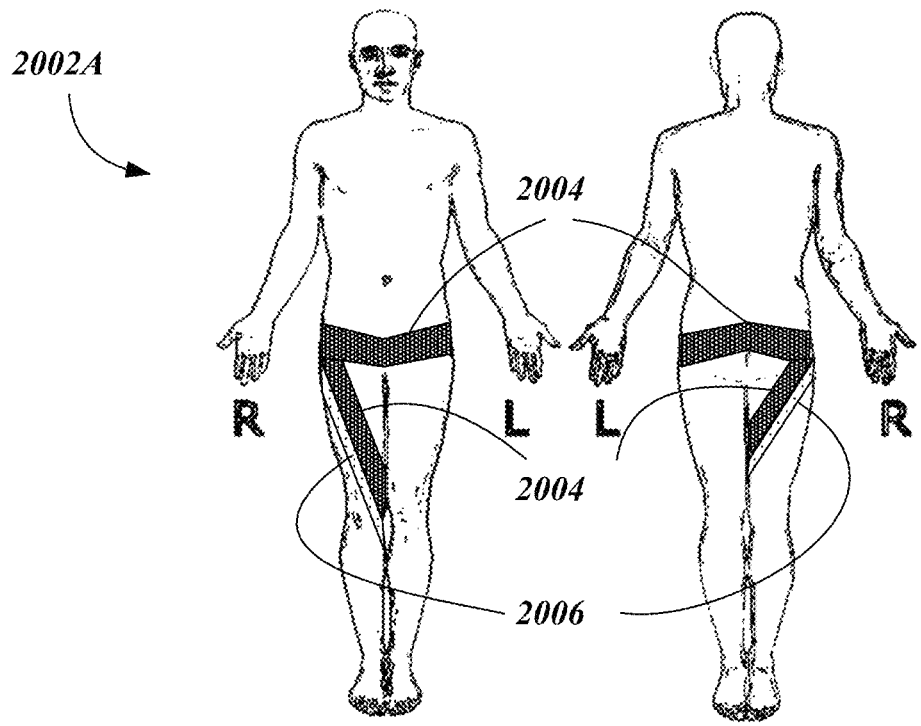
FIGS. 20A-20C are diagrams illustrating GUI interactive displays with active elements for specifying and displaying therapy type selections according to some embodiments.
Figure 20B:
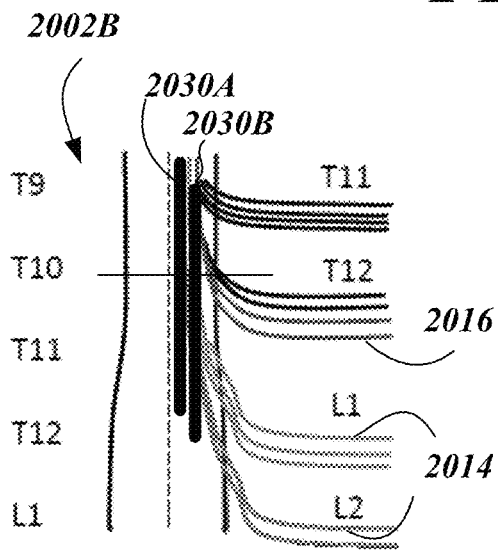
Figure 20C:
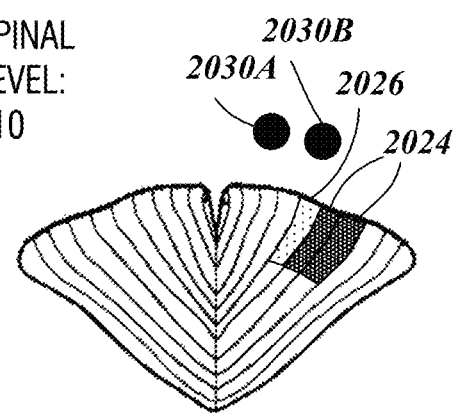

FIGS. 20A-20C illustrate GUI interactive displays with active elements 2002A-2002C for specifying and displaying therapy type selections according to some embodiments. The GUI interactive displays of FIGS. 20A-20C may be implemented as another type of neuromodulation control of sensation-targeting input 1806 and anatomy-targeting input 1808, as well as graphical display 1814, in which therapy-type selection is facilitated. In some embodiments, the GUI interactive displays of FIGS. 20A-20C are selectable as a further type of neuromodulation control in addition to the controls of FIGS. 19A-19C. In one such embodiment, the GUI displays and user inputs may be toggled between the pain-treatment control of FIGS. 19A-19C and the therapy-type selection of FIGS. 20A-20C.

Notably, in some embodiments, neuromodulation-type selection input may be used in conjunction with pain-location selection input. In one such example, a selected type of neuromodulation is applied to target regions that are specified conjunctively (i.e., intersecting) by GUI elements 1902A-C and 2002A-C.

GUI elements 2002A include graphical selectable portions of the anatomic map for which therapy type may be specified. As depicted, regions 2004 may be designated for a first type of neuromodulation (e.g., paresthesia), while regions 2006 may be specified for a second type of neuromodulation (e.g., sub-threshold therapy). Other types of neuromodulation that may be specified according to various embodiments include exclusion (e.g., an absence of neuromodulation, or suppressive neuromodulation to counteract other neuromodulation that may be applied in a neighboring vicinity), priming, or other known types or types to be developed in the future.

FIGS. 20B and 20C are diagrams illustrating additional GUI displays showing posterior-view, and sectional portions of the dorsal column, respectively, including active elements 2002B and 2002C. In a related embodiment, as illustrated, electrode arrangements 2030A and 2030B are shown in the displays of FIGS. 20B and 20C. In the GUI display depicted FIG. 20B, highlighted dorsal roots 2014 and 2016 are highlighted respectively according to the neuromodulation therapy type region selections 2004, 2006 made using active elements 2002A. Similarly, in the GUI display depicted in FIG. 20C, dorsal column portions corresponding to the therapy type region selections 2004, 2006, namely, regions 2024 and 2026, are similarly highlighted in response to the selections. In related embodiments, selections of therapy type may also be made via user interaction with active elements 2002B and 2002C, in which case the highlighted portions of the various views are updated to reflect the selections. In a related embodiment, targeting selector 1830 and neuromodulation parameter selector 1832 are passed commands relating to the therapy type selections made via active elements 2002A-2002C and respectively respond to the commands by setting or adjusting the neuromodulation targeting and signaling.

Figure 21:
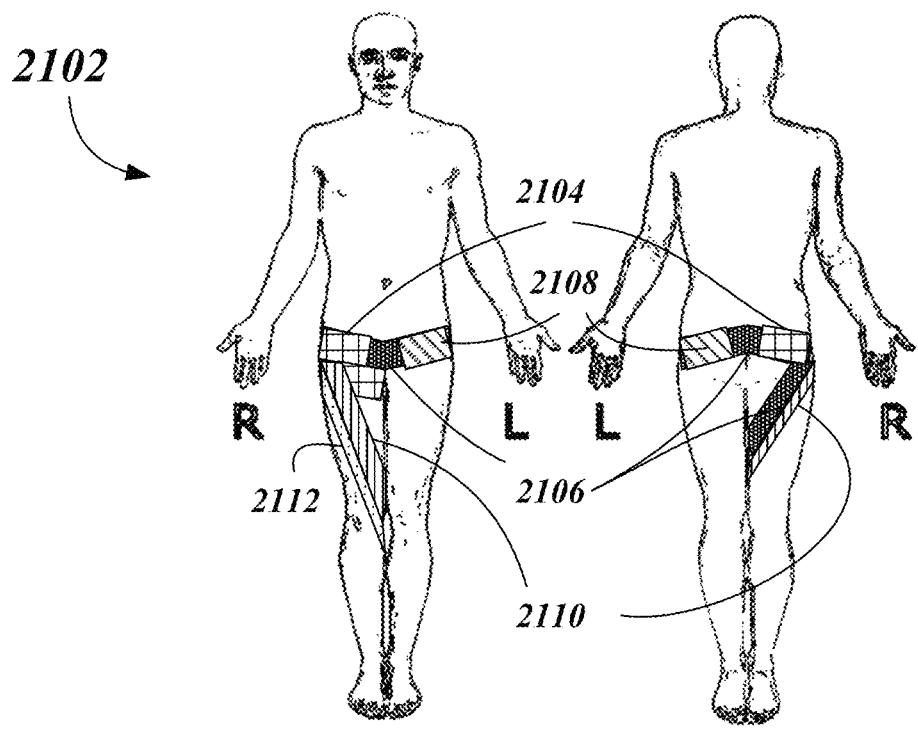
FIG. 21 is a diagram illustrating an example GUI-based implementation of a patient feedback input and graphical display according to an example embodiment.

FIG. 21 is a diagram illustrating an example GUI-based implementation of patient feedback input 1810 and graphical display 1814 according to an example embodiment. As illustrated, active elements 2102 facilitate user selection of portions of the body, along with inputs to indicate sensations experienced by the patient. In the example depicted, regions 2104-2112 are differentially highlighted to indicate different sensations. As an example, the following sensations may be input: paresthesia 2104, no paresthesia 2106, pain relief without paresthesia 2108, pain relief with paresthesia 2110, and continued pain without discernible effect of neuromodulation 2112. In a related embodiment, active elements 2102 are displayed in response to user-controlled toggling between active elements 1902A-1902C (FIG. 19), 2002A-2002C (FIG. 20), and active elements The patient feedback input is provided to targeting selector 1830 and neuromodulation parameter selector 1832, each of which may respectively control the targeting and administration of neuromodulation therapy to meet the intended therapy objectives specified using active elements 1902A-C, 2002A-C, or some combination thereof.

Figure 22A:
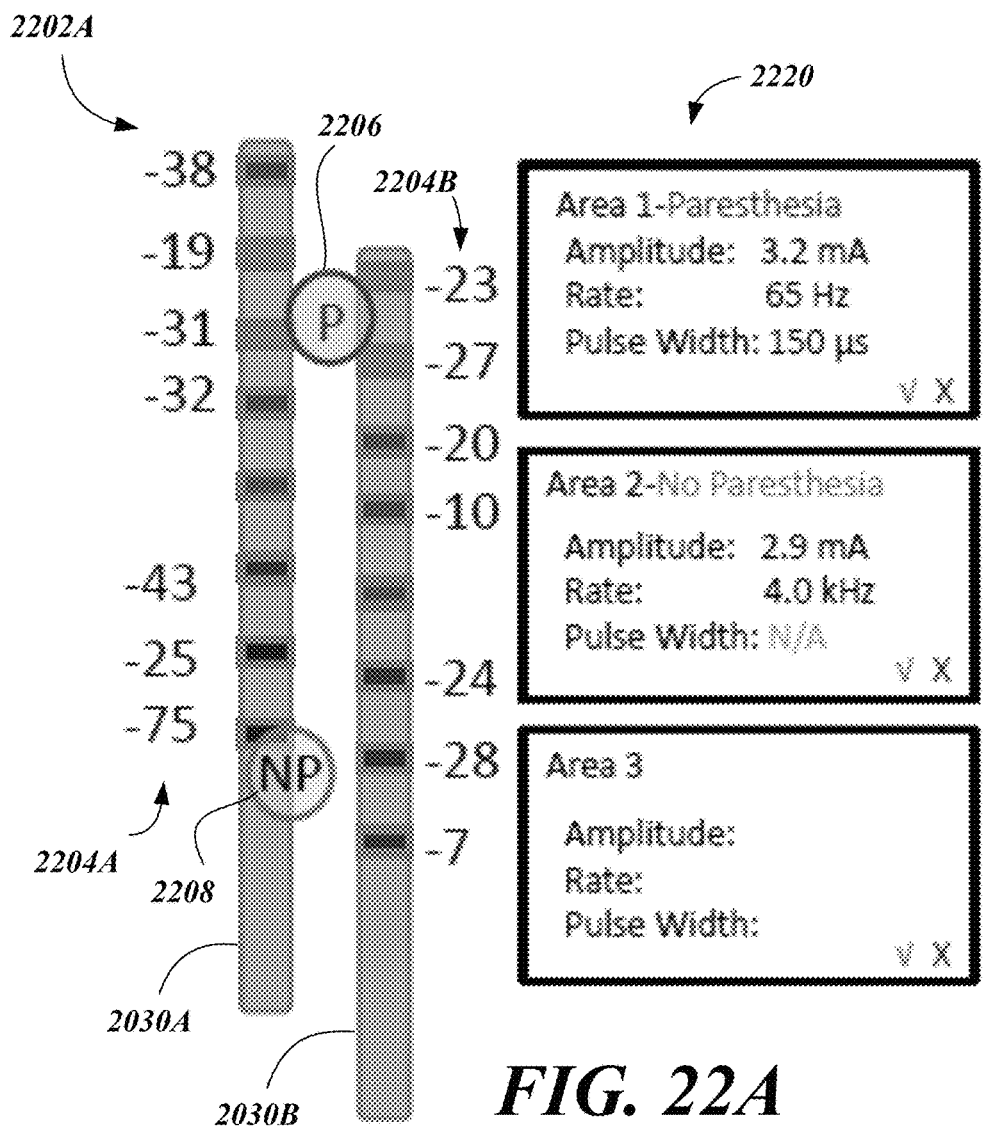
FIGS. 22A-22C are diagrams illustrating an example GUI implementation of a manual-mode input and graphical display according to an embodiment.
Figure 22B:
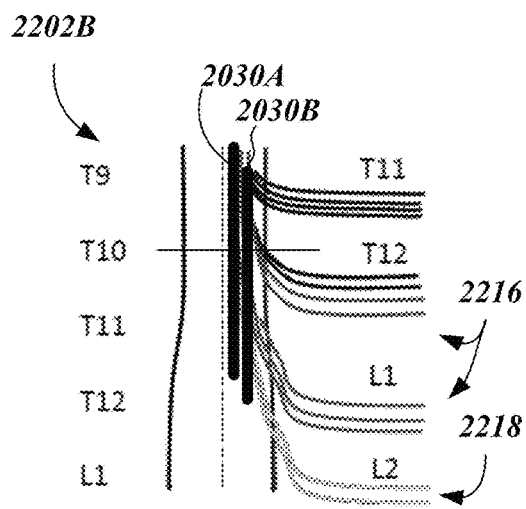
Figure 22C:
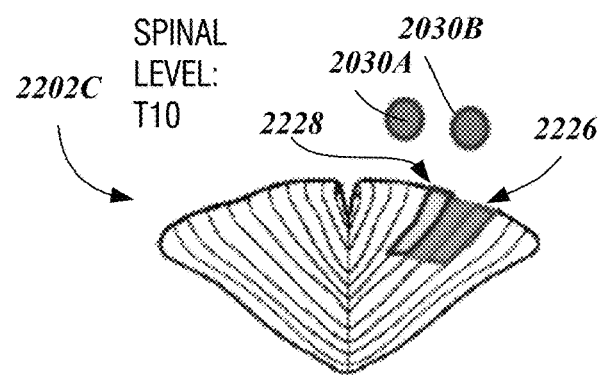

FIGS. 22A-22C are diagrams illustrating an example GUI implementation of manual-mode input 1812 and graphical display 1814 according to an embodiment. Referring to FIG. 22A, electrode arrangements 2030A and 2030B are displayed along with active elements 2202A, which include electrode polarity and intensity controls 2204A and 2204B, which provide for entry of numerical values. In addition, target regions may be placed. In a related embodiment, therapy type may be specified as well. As depicted in the present example, a first target region with paresthesia neuromodulation therapy P is indicated at 2206; whereas a second target region with non-paresthesia neuromodulation therapy NP is indicated at 2208. In addition, neuromodulation parameters may be specified with inputs 2210 as shown, where Area 1 corresponds to the first target region, and Area 2 corresponds to the second target region. Notably, the manual control of the GUI of FIG. 22A is not an anatomic-specific input. Rather, it is a spatial input with a frame of reference relative to the electrode arrangements 2030A and 2030B.

FIGS. 20B and 20C are diagrams illustrating GUI displays showing posterior-view, and sectional portions of the dorsal column, respectively, including active elements 2202B and 2202C. In a related embodiment, as illustrated, electrode arrangements 2030A and 2030B are shown in these example displays. In the GUI of FIG. 22B, dorsal roots are highlighted at 2216 and 2218 to indicate the administration of neuromodulation therapy at the corresponding sites of the dorsal column. Active elements 2202B may be manipulated by the user to set or adjust the location of the neuromodulation therapy targeting. Similarly, in the GUI of FIG. 22C, portions of the dorsal column section are highlighted, as indicated at 2226 and 2228, according to the specified type of neuromodulation therapy via active elements 2202A, 2202B, or 2202C. In this example, highlighted portion 2226 corresponds to paresthesia neuromodulation therapy P 2206, and highlighted portion 2228 corresponds to non-paresthesia neuromodulation therapy 2208.

Notably, in the GUIs of FIGS. 22B and 22C, the target region for neuromodulation therapy is essentially the same as the anatomic-specific input. This case may be contrasted with the anatomic input of the GUIs of FIGS. 19A and 20A, where the anatomic-specific input (e.g., locations where the neuromodulation objection is to be felt in those cases) are at distinct locations from where the corresponding neuromodulation is to be targeted.

Referring again to FIG. 18, in response to the user's selection of neuromodulation therapy location, the location of the effect of the neuromodulation, and neuromodulation objective, whether it is paresthesia, or non-paresthesia pain relief, or other objective, neuromodulation delivery controller 1835 operates to computationally determine an electrode configuration and neuromodulation signaling to achieve the desired effect. To this end, in the embodiment depicted, databases 1822-1828 are utilized in conjunction with targeting selector 1830, and neuromodulation parameter selector 1822.

Spinal/dermatomal map database 1822 contains general anatomic information that associates regions of the body where pain is felt and where the effects of neuromodulation therapy may be felt. Spinal/dermatomal map database 1822 may include associations between parts of the dorsal column, dorsal roots, and nerve tracts extending and branching therefrom, to the peripheries of the body. In a related embodiment, spinal/dermatomal map database 1822 includes neurologic structural information, such as the size and shape of nerve fibers and other structures, as well as electrostimulation-relevant data such as activating function information, and the like.

Spatial targeting criteria database 1824 includes decision logic, parameter values, formulas, neurologic activating function information, genetic algorithm fitness function information, fitness function weighting, criteria for variation of fitness function weighting, patient feedback weighting, sensed biomarker weighting, sensed electrical parameter weighting, and other related parameters applicable to computational determination of electrode configurations by targeting selector 1830 to achieve neuromodulation therapy objectives established via operation of the GUI 1804.

Parameter setting criteria database 1826 contains decision logic, parameter values, formulas, neurologic activating function information, genetic algorithm fitness function information, fitness function weighting, criteria for variation of fitness function weighting, patient feedback weighting, sensed biomarker weighting, sensed electrical parameter weighting, and other related parameters applicable to computational determination of neuromodulation signaling by neuromodulation parameter selector 1832 to achieve neuromodulation therapy objectives established via operation of the GUI 1804, and based on targeting selection made by targeting selector 1830.

Patient-specific physiology database 1828 contains details specific to the patient, such as radiologic information (e.g., magnetic-resonance imaging (MRI) data, computer-tomography (CT) data, ultrasound imaging data, X-ray or contrast-assisted X-ray data, photographic or video-captured data (e.g., endoscopically or arthroscopically obtained), or other data about the patient's physiology obtained by measurement of the patient using any suitable modality. In a related embodiment, therapy configurator 1802 includes a patient-anatomy data synthesis engine (not shown) that is constructed, programmed, or otherwise configured, to incorporate the patient-specific physiology data from database 1828 with the spinal/dermatomal map data from database 1822 such that, where available, the patient-specific physiology data of database 1828 is used preferentially over the non-specific data of database 1822, with the latter being used for default physiology information where patient-specific data is absent or lacking in sufficient detail. In a related embodiment, the patient-anatomy data synthesis engine may include a data normalization engine that interprets the patient-specific physiology data, and converts portions of it into a format consistent with the spinal/dermatomal map data format.

According to various embodiments, targeting selector 1830 of neuromodulation delivery controller 1835 may use "target multipoles" to provide a linear field that may maximize the electric field in a region while minimizing the activation of dorsal columns. These target multipoles may be referred to as "ideal" or "virtual" multipoles. Each target pole of a target multipole may correspond to one physical electrode, but may also correspond to a space that does not correspond to one electrode, and may be emulated using electrode fractionalization. By way of examples, U.S. Pat. Nos. 8,412,345 and 8,909,350 describe target multipoles. U.S. Pat. Nos. 8,412,345 and 8,909,350 are hereby incorporated by reference. Target multipoles are briefly described herein.

A stimulation target in the form of a target poles (e.g., a target multipole such as a target bipole or target tripole or a target multipole with more than three target poles) may be defined and the stimulation parameters, including the fractionalized current values on each of the electrodes, may be computationally determined in a manner that emulates these target poles. Current steering may be implemented by moving the target poles about the leads, such that the appropriate fractionalized current values for the electrodes are computed for each of the various positions of the target pole.

Figure 23A:
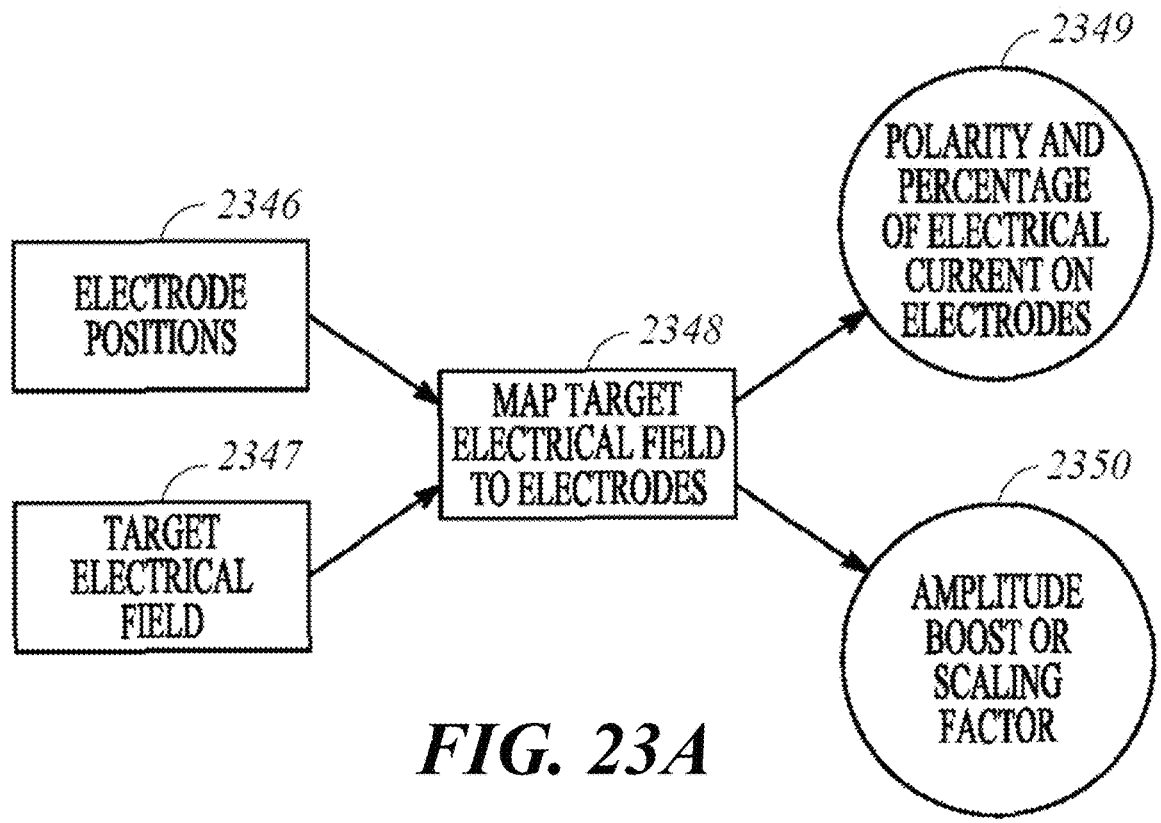
FIG. 23A is a diagram illustrating an example operation of a neuromodulation delivery controller according to an embodiment.

With reference to FIG. 23A, neuromodulation delivery controller 1835 may be configured to accept relative electrode positions 2346 and a representation of an target electrical field 2347 (instead of including these parameters in the design of navigation tables) and maps the target electrical field to the electrodes 2348, thereby yielding the polarities and percentages of electrical current to be associated with the electrodes 2349, as well as a boost or scaling factor 2350 for globally adjusting the magnitude of the total current supplied to the electrodes to maintain a perceived intensity level of the electrical stimulation. Electrode locations and information about the desired electrical field may be independently inputted into the algorithm.

Figure 23B:
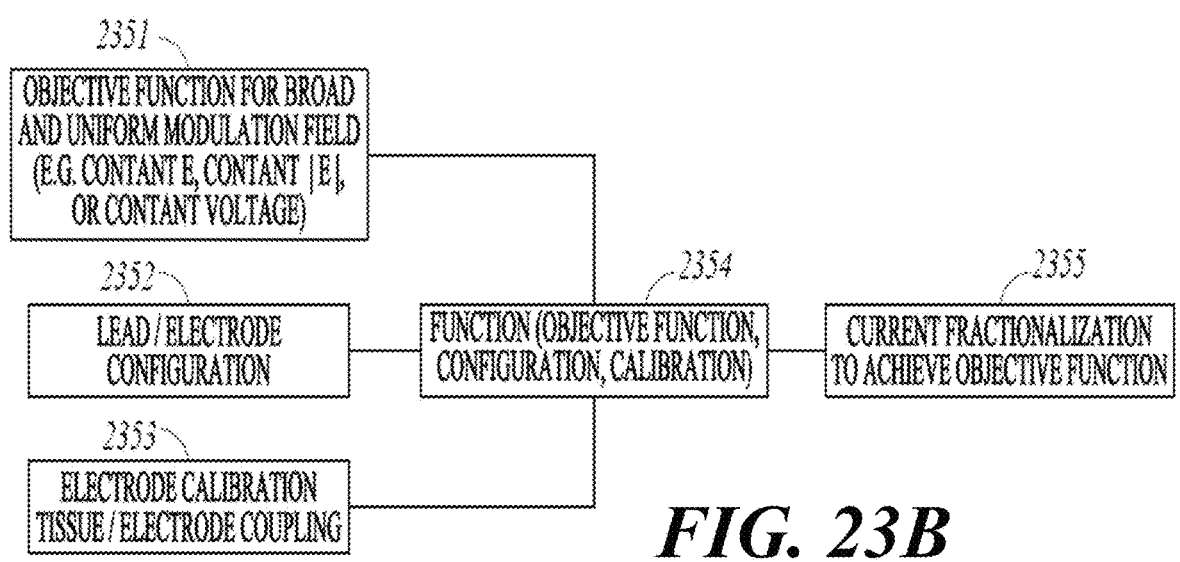
FIG. 23B is a diagram illustrating a process for determining fractionalization to achieve an objective function using a neuromodulation delivery controller according to some embodiments.

FIG. 23B illustrates, by way of example, an embodiment for determining fractionalization to achieve an objective function. An objective function refers to a function with desirable characteristics for modulating the targeted tissue. The objective function may also be referred to as an objective target function. An objective function 2351 for a broad and uniform modulation field is identified for a given volume of tissue. Examples of an objective function includes a constant E (electric field), a constant |E| (electric field magnitude), and a constant voltage. The lead and electrode configuration 2352 are also identified, as well as calibration for electrode tissue coupling 2353. A function 2354 is performed that is dependent on the objective function, the lead and electrode configuration and the calibration. The result of the function is the fractionalization of modulation energy (e.g. current) 2355 for each electrode to achieve the objective function.

Figure 24:
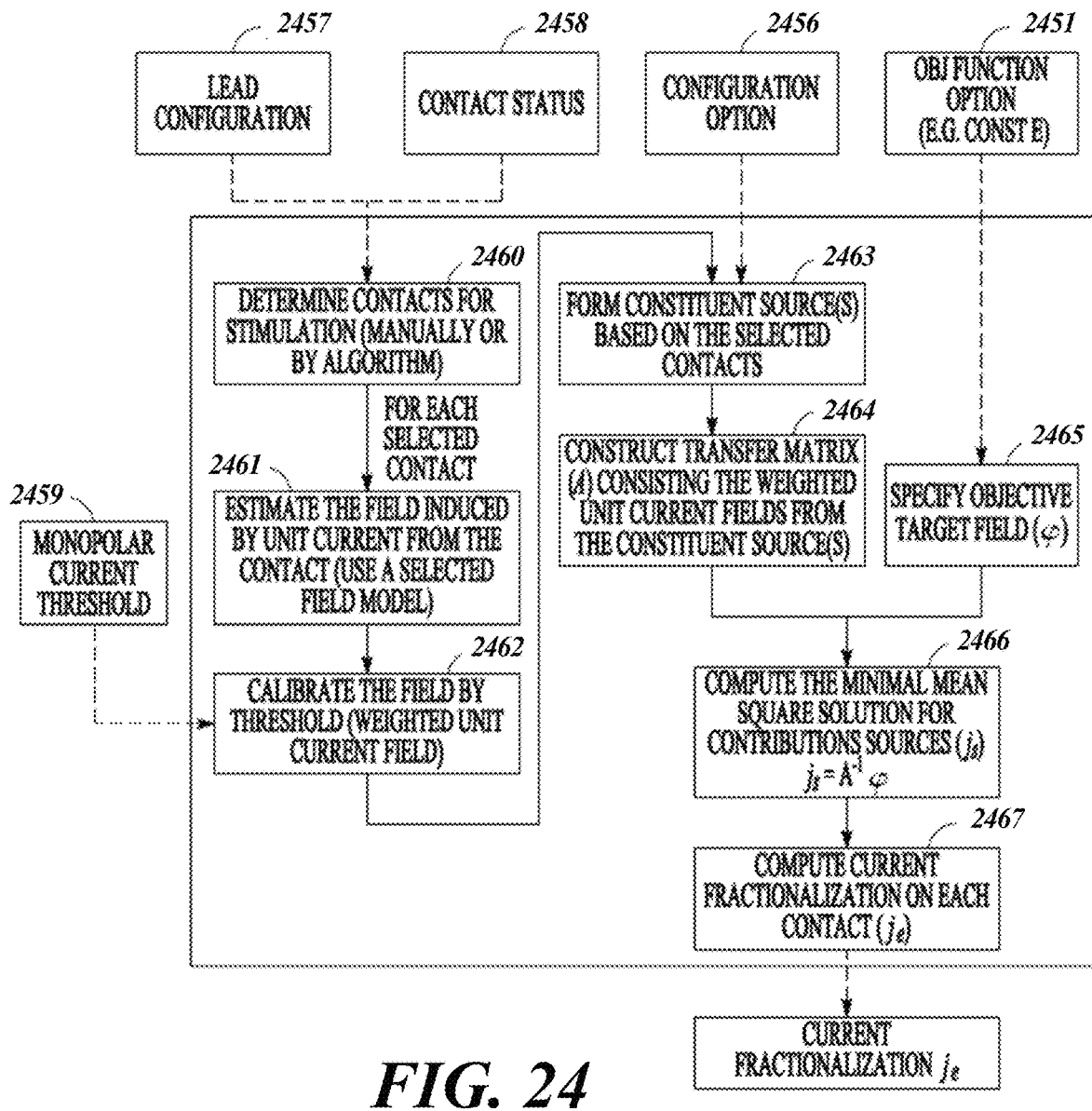
FIG. 24 illustrates, by way of example, an embodiment for determining fractionalization to achieve an objective function, in greater detail.

FIG. 24 illustrates, by way of example, an embodiment for determining fractionalization to achieve an objective function with more detail. An objective target function 2451 (e.g. constant E) is provided as an input to a process. Other inputs to the process include a configuration option 2456, a lead configuration 2457 and electrode contact status 2458, and a threshold 2459 such as a current threshold or more particularly a monopolar current threshold. The lead configuration 2457 and contact status 2458 identify an electrode arrangement, identifying a position of each electrode to determine the field. The overall field is a superimposed field from each electrode. The configuration option 2456 refers to monopolar (same polarity for all activated electrodes) and multipolar options (combined anode and cathodes in field). The threshold is used to compensate for electrode/tissue coupling differences.

The contacts for stimulation may be determined automatically or manually 2460 from the lead configuration and contact status. A selected field model may be used to estimate the field induced by unit current from the contact 2461. The field is calibrated using the threshold 2462. For example, the unit current field may be weighted. Constituent forces are formed based on the selected contacts 2463, and a transfer matrix 2464 is constructed to use to compute the minimal mean square solution 2466 using contributions from the constituent sources and using a specified target field 2465. The solution can be used to compute the current fractionalization on each contact 2467.

With reference to FIGS. 25A-25B, neuromodulation delivery controller 1835 may map a target electrical field to the electrode array by estimating the field potential values (or some other linear electrical parameter, such as an activating function, current density, etc.) of the target field at a plurality of spatial observation points, which are associated with anatomic structures that constitute the neuromodulation target regions. Neuromodulation delivery controller 1835 may accomplish this by determining the desired locations of target current source poles relative to the electrode array, and modeling an electrical field generated by the target current source poles to determine desired field potential values at the spatial observation points (e.g., using analytical and/or numerical models).

Although target current source poles are one way to represent a "target electrical field", other representations of target fields may be used. The locations of the target current source poles may be determined in a manner that places the resulting electrical field over an identified target region of the patient. The spatial observation points may be spaced or otherwise arranged in a manner that would, at the least, cover the determined target regions to be stimulated and avoid any specified or determined regions that should not be stimulated. The locations of the target current source poles may be determined automatically based on the commands provided via GUI 1804, and may be displayed to the user along with the electrode locations, may be determined based on electrical measurements taken at the electrodes by sensor system 1840 (FIG. 18), in combination with the information represented in databases 1822-1828.

In various embodiments, sensor system 1840 may capture electrical measurements representing electric fields, currents, or other measurements of the applied neuromodulation therapy. In related embodiments, sensor system 1840 may capture biomarker information, such as depolarization, hyperpolarization, paresthesia or sub-perception biomarkers. Sensor system 1840 may be used to provide feedback to neuromodulation delivery controller 1835 so that the neuromodulation targeting and signaling may be controlled or adjusted to meet treatment objectives.

Referring to FIGS. 26A-26C, neuromodulation delivery controller 1835 may automatically select a plurality of constituent current sources at the locations of the electrodes. The locations of the electrodes may be determined based on measurements taken at the electrodes in response to sub-threshold electrical signals transmitted between the electrodes. In the illustrated target bipole a first constituent current source can be defined at the locations of electrodes E1 and E2 as −100% and +100%, respectively (FIG. 26A); a second constituent current source can be defined at the locations of electrodes E2 and E3 as −100% and +100%, respectively (FIG. 26B); a third constituent current source can be defined at the locations of electrodes E3 and E4 as −100% and +100%, respectively (FIG. 26C); and so on. The location of each of the electrodes is included within at least one of the constituent sources. Thus, the minimum number of constituent sources may be equal to the number of contacts less one, or may equal the number of contacts (e. g., if a monopole is used as the constituent source).

Once the constituent sources are selected, neuromodulation delivery controller 1835 may determine the relative strengths of the constituent current sources that, when combined, result in estimated electrical field potential values at the spatial observation points that best matches the desired field potential values at the spatial observation points, which may be associated with particular portions of the dorsal column. In particular, neuromodulation delivery controller 1835 may model the constituent current sources (e.g., using analytical and/or numerical models) and estimate the field potential values per unit current (V/mA) generated by each of the constituent current sources at the spatial observation points, and may generate an m×n transfer matrix from the estimated field potential values per unit current, with m equaling the number of spatial observation points and n equaling the number of constituent sources. The relative strengths of the constituent current sources may be determined using an optimization function that includes the transfer matrix A and the desired field potential values.

The optimization function may be a least-squares (overdetermined) function expressed as: $|\varphi-A\hat{j}|2$, where $\varphi$ is an m-element vector of the desired field potential values, A is the transfer matrix, and $\hat{j}$ is an n-element vector of the strengths of the constituent current sources. The constituent current source strengths j may be solved such that the optimization function $|\varphi-A\hat{j}|^2$ is minimized. The square difference is minimized if $\varphi=A\hat{j}$. One approach for solving this problem may be to invert the transfer matrix A and pre-multiply, such that $A^{-1}=\varphi A^{-1}A\hat{j}$, which yields the solution $j=A^{-1}\varphi$. Once the strengths of the constituent current sources are determined, neuromodulation delivery controller 1835 converts these strengths to current distributions on the electrodes in the form of a polarity and percentage.

In a related embodiment, neuromodulation delivery controller 1835 is configured to optimize neuromodulation therapy to be administered by calculating electric fields or activating functions along target regions (e.g., fiber tracts) and placing multipoles to maximize the number of fiber tracts that cross the field to receive the neurostimulation above a defined threshold value to meet the treatment objectives. In another related embodiment, activating functions are re-derived for dorsal root tracts having particular features, such as bends, entries into the spinal cord, and others, that impact the threshold for activation. For instance, activating functions may be recalculated to take into account fibers entering the spinal cord, and at branch points, at turns, etc. In addition, the size and shape of target tissue may also be taken into account for determining targeting, waveform, and amplitude parameters. In another related embodiment, the relative angles between the multipole(s) and target regions may also be taken into account in determining the activating functions and corresponding neuromodulation signal parameters.

In another related embodiment, a fitness function that takes into account various anatomic and treatment-objective parameters is applied in the control of the neuromodulation targeting and signaling control. For instance, a fitness function may define anatomic structures to be stimulated and anatomic structures to be avoided. Likewise, certain structures may be targeted for paresthesia, while others may be targeted for sub-threshold stimulation. A weighting function may be applied with corresponding weights assigned to the various determined objectives based on the commands obtained via GUI 1804. Patient feedback and sensed parameters may be fed to the fitness function for control and optimization.

In addition to the Examples discussed in the Summary Section above, some other non-limiting examples are provided as follows.

Example 1 is a neuromodulation targeting system facilitating spatial selection of a neuromodulation objective, the system comprising: a graphical user interface (GUI) that includes an interactive display representing anatomy of a patient with user-selectable anatomic-specific inputs associated with a plurality of predefined neural pathways corresponding to distinct localized clinical effects of neuromodulation; and a targeting selector engine operatively coupled with the GUI, the targeting selector engine being responsive to user selection of a first anatomic-specific input to: computationally determine a first target region where neuromodulation therapy is to be directed, the first target region being distinct from an anatomic location of the anatomic-specific input, and configure delivery of the neuromodulation therapy to the first target region to produce a first localized clinical effect in the patient at a location corresponding to the first anatomic-specific input, upon administration of the neuromodulation therapy to the patient, to achieve the neuromodulation objective.

In Example 2, the subject matter of Example 1 optionally includes wherein the first target region is a neuroanatomic region selected from the group consisting of: a dorsal column region, a dorsal root region, a dorsal horn region, a dermatomic region, or any combination thereof.

In Example 3, the subject matter of any one or more of Examples 1-2 optionally include wherein the plurality of predefined neural pathways corresponding to distinct localized clinical effects of neuromodulation include dermatomes.

In Example 4, the subject matter of any one or more of Examples 1-3 optionally include wherein the first anatomic-specific input represents a site where pain is reported by the patient.

In Example 5, the subject matter of any one or more of Examples 1-4 optionally include wherein the interactive display representing anatomy of the patient includes a dermatomal map of the patient with individually-selectable dermatomes.

In Example 6, the subject matter of any one or more of Examples 1-5 optionally include wherein the interactive display representing anatomy of the patient further includes a spinal map of the patient with selectable portions of dorsal roots.

In Example 7, the subject matter of any one or more of Examples 1-6 optionally include wherein the interactive display representing anatomy of the patient includes a map of fiber tracts proximate the spinal cord with selectable portions of the fiber tracts.

In Example 8, the subject matter of any one or more of Examples 1-7 optionally include wherein the interactive display representing the anatomy of the patient is based on actual measured anatomic characteristics of the patient.

In Example 9, the subject matter of any one or more of Examples 1-8 optionally include wherein the interactive display further includes a therapy type selector input facilitating selection of neuromodulation type from among paresthesia neuromodulation, and sub-perception neuromodulation.

In Example 10, the subject matter of Example 9 optionally includes wherein the interactive display further facilitates selection of an exclusion zone of the anatomy of the patient that is to be free of certain types of neuromodulation, as may be user-specified.

In Example 11, the subject matter of any one or more of Examples 1-10 optionally include an electrotherapy parameter selector engine configured to determine an electrical signal waveform to be applied to the first target region, the electrical signal waveform being specific to a neurologic structure present at the first target region.

In Example 12, the subject matter of Example 11 optionally includes wherein the electrotherapy parameter selector engine is further configured to determine the electrical signal waveform based on an activation function associated with the neurologic structure at the first target region.

In Example 13, the subject matter of Example 12 optionally includes wherein the electrotherapy parameter selector engine is configured to determine the electrical signal waveform based on an orientation of the neurologic structure at the first target region relative to a location of a set of electrodes from which the neuromodulation therapy is to be directed.

In Example 14, the subject matter of any one or more of Examples 11-13 optionally include wherein the GUI includes a treatment objective input to accept a clinical effect objective specified by a user; and wherein the electrotherapy parameter selector engine is further configured to determine the electrical signal waveform based on the clinical effect objective.

In Example 15, the subject matter of any one or more of Examples 1-14 optionally include wherein the first localized clinical effect includes pain relief.

In Example 16, the subject matter of any one or more of Examples 1-15 optionally include wherein the first localized clinical effect includes paresthesia.

Example 17 is a neuromodulation targeting system facilitating spatial selection of a neuromodulation objective, the system comprising: user-input means for providing user-selectable anatomic-specific inputs via an interactive display representing anatomy of a patient and associated with a plurality of predefined neural pathways corresponding to distinct localized clinical effects of neuromodulation; and neuromodulation targeting means responsive to user selection of a first anatomic-specific input to via the user-input means, the neuromodulation targeting means comprising: means for determining a first target region where neuromodulation therapy is to be directed, the first target region being distinct from an anatomic location of the anatomic-specific input, and means for configuring delivery of the neuromodulation therapy to the first target region to produce a first localized clinical effect in the patient at a location corresponding to the first anatomic-specific input, upon administration of the neuromodulation therapy to the patient, to achieve the neuromodulation objective.

In Example 18, the subject matter of Example 17 optionally includes wherein the first target region is a neuroanatomic region selected from the group consisting of: a dorsal column region, a dorsal root region, a dorsal horn region, a dermatomic region, or any combination thereof.

In Example 19, the subject matter of any one or more of Examples 17-18 optionally include wherein the plurality of predefined neural pathways corresponding to distinct localized clinical effects of neuromodulation include dermatomes.

In Example 20, the subject matter of any one or more of Examples 17-19 optionally include wherein the first anatomic-specific input represents a site where pain is reported by the patient.

In Example 21, the subject matter of any one or more of Examples 17-20 optionally include wherein the interactive display representing anatomy of the patient includes a dermatomal map of the patient with individually-selectable dermatomes.

In Example 22, the subject matter of any one or more of Examples 17-21 optionally include wherein the interactive display representing anatomy of the patient further includes a spinal map of the patient with selectable portions of dorsal roots.

In Example 23, the subject matter of any one or more of Examples 17-22 optionally include wherein the interactive display representing anatomy of the patient includes a map of fiber tracts proximate the spinal cord with selectable portions of the fiber tracts.

In Example 24, the subject matter of any one or more of Examples 17-23 optionally include wherein the interactive display representing the anatomy of the patient is based on actual measured anatomic characteristics of the patient.

In Example 25, the subject matter of any one or more of Examples 17-24 optionally include wherein the interactive display further includes a therapy type selector input facilitating selection of neuromodulation type from among paresthesia neuromodulation, and sub-perception neuromodulation.

In Example 26, the subject matter of Example 25 optionally includes wherein the interactive display further facilitates selection of an exclusion zone of the anatomy of the patient that is to be free of one or more specified types of neuromodulation, or of all neuromodulation.

In Example 27, the subject matter of any one or more of Examples 17-26 optionally include electrotherapy parameter selecting means for determining an electrical signal waveform to be applied to the first target region, the electrical signal waveform being specific to a neurologic structure present at the first target region.

In Example 28, the subject matter of Example 27 optionally includes wherein the electrotherapy parameter selecting means are further configured to determine the electrical signal waveform based on an activation function associated with the neurologic structure at the first target region.

In Example 29, the subject matter of Example 28 optionally includes wherein the electrotherapy parameter selecting means are configured to determine the electrical signal waveform based on an orientation of the neurologic structure at the first target region relative to a location of a set of electrodes from which the neuromodulation therapy is to be directed.

In Example 30, the subject matter of any one or more of Examples 27-29 optionally include wherein the user-input means include a treatment objective input to accept a clinical effect objective specified by a user; and wherein the electrotherapy parameter selecting means are further configured to determine the electrical signal waveform based on the clinical effect objective.

In Example 31, the subject matter of any one or more of Examples 17-30 optionally include wherein the first localized clinical effect includes pain relief.

In Example 32, the subject matter of any one or more of Examples 17-31 optionally include wherein the first localized clinical effect includes paresthesia.

Example 33 is in a neuromodulation targeting system, a method for facilitating spatial selection of a neuromodulation objective, the method comprising: providing a graphical user interface (GUI) that includes an interactive display representing anatomy of a patient with user-selectable anatomic-specific inputs associated with a plurality of predefined neural pathways corresponding to distinct localized clinical effects of neuromodulation; and responding to user selection of a first anatomic-specific input, including: computationally determining a first target region where neuromodulation therapy is to be directed, the first target region being distinct from an anatomic location of the anatomic-specific input, and configuring the neuromodulation therapy for delivery to the first target region to produce a first localized clinical effect in the patient at a location corresponding to the first anatomic-specific input, upon administration of the neuromodulation therapy to the patient, to achieve the neuromodulation objective.

In Example 34, the subject matter of Example 33 optionally includes wherein the first target region is a neuroanatomic region selected from the group consisting of: a dorsal column region, a dorsal root region, a dorsal horn region, a dermatomic region, or any combination thereof.

In Example 35, the subject matter of any one or more of Examples 33-34 optionally include wherein the plurality of predefined neural pathways corresponding to distinct localized clinical effects of neuromodulation include dermatomes.

In Example 36, the subject matter of any one or more of Examples 33-35 optionally include wherein the first anatomic-specific input represents a site where pain is reported by the patient.

In Example 37, the subject matter of any one or more of Examples 33-36 optionally include wherein the interactive display representing anatomy of the patient includes a dermatomal map of the patient with individually-selectable dermatomes.

In Example 38, the subject matter of any one or more of Examples 33-37 optionally include wherein the interactive display representing anatomy of the patient further includes a spinal map of the patient with selectable portions of dorsal roots.

In Example 39, the subject matter of any one or more of Examples 33-38 optionally include wherein the interactive display representing anatomy of the patient includes a map of fiber tracts proximate the spinal cord with selectable portions of the fiber tracts.

In Example 40, the subject matter of any one or more of Examples 33-39 optionally include wherein the interactive display representing the anatomy of the patient is based on actual measured anatomic characteristics of the patient.

In Example 41, the subject matter of any one or more of Examples 33-40 optionally include wherein the interactive display further includes a therapy type selector input facilitating selection of neuromodulation type from among paresthesia neuromodulation, and sub-perception neuromodulation.

In Example 42, the subject matter of Example 41 optionally includes wherein the interactive display further facilitates selection of an exclusion zone of the anatomy of the patient that is to be free of certain one or more types of neuromodulation, as may be specified.

In Example 43, the subject matter of any one or more of Examples 33-42 optionally include determining an electrical signal waveform to be applied to the first target region, the electrical signal waveform being specific to a neurologic structure present at the first target region.

In Example 44, the subject matter of Example 43 optionally includes determining the electrical signal waveform based on an activation function associated with the neurologic structure at the first target region.

In Example 45, the subject matter of Example 44 optionally includes determining the electrical signal waveform based on an orientation of the neurologic structure at the first target region relative to a location of a set of electrodes from which the neuromodulation therapy is to be directed.

In Example 46, the subject matter of any one or more of Examples 43-45 optionally include wherein the GUI includes a treatment objective input to accept a clinical effect objective specified by a user; further comprising: determining the electrical signal waveform based on the clinical effect objective.

In Example 47, the subject matter of any one or more of Examples 33-46 optionally include wherein the first localized clinical effect includes pain relief.

In Example 48, the subject matter of any one or more of Examples 33-47 optionally include wherein the first localized clinical effect includes paresthesia.

The above detailed description is intended to be illustrative, and not restrictive. The scope of the disclosure should, therefore, be determined with references to the appended claims, along with the full scope of equivalents to which such claims are entitled.

What is claimed is:

1. A neuromodulation targeting system facilitating spatial selection of a neuromodulation objective for a neuromodulation therapy to be delivered by a neuromodulation device, the system comprising:
   a graphical user interface (GUI) that includes an interactive display representing anatomy of a patient with user-selectable anatomic sites associated with a plurality of predefined neural pathways corresponding to distinct localized clinical effects of neuromodulation, wherein the interactive display includes at least one of a dermatomal map of the patient with individually-selectable dermatomes, a spinal map of the patient with selectable portions of dorsal roots, or a map of fiber tracts proximate the spinal cord with selectable portions of the fiber tracts; and
   a targeting selector engine operatively coupled with the GUI, the targeting selector engine being responsive to user selection of a first anatomic site to:
   computationally determine a first target region where the neuromodulation therapy is to be directed, the first target region being distinct from an anatomic location corresponding to the user-selected first anatomic site, and
   configure delivery of the neuromodulation therapy by the neuromodulation device to the first target region to produce a first localized clinical effect in the patient at the anatomic location corresponding to the user-selected first anatomic site, upon administration of the neuromodulation therapy to the patient, to achieve the neuromodulation objective,
   wherein the interactive display further includes a therapy type selector input facilitating a user-selection of neuromodulation type for each selected site from the user-selectable anatomic sites, the user-selection of neuromodulation type including a user-selection from among paresthesia neuromodulation and sub-perception neuromodulation.

2. The neuromodulation targeting system of claim 1, wherein the first target region is a neuroanatomic region selected from the group consisting of: a dorsal column region, a dorsal root region, a dorsal horn region, a dermatomic region, or any combination thereof.

3. The neuromodulation targeting system of claim 1, wherein the plurality of predefined neural pathways corresponding to distinct localized clinical effects of neuromodulation include dermatomes.

4. The neuromodulation targeting system of claim 1, wherein the first anatomic site represents a site where pain is reported by the patient.

5. The neuromodulation targeting system of claim 1, wherein the interactive display representing anatomy of the patient includes the dermatomal map of the patient with individually-selectable dermatomes.

6. The neuromodulation targeting system of claim 1, wherein the interactive display representing anatomy of the patient further includes the spinal map of the patient with selectable portions of dorsal roots.

7. The neuromodulation targeting system of claim 1, wherein the interactive display representing anatomy of the patient includes the map of fiber tracts proximate the spinal cord with selectable portions of the fiber tracts.

8. The neuromodulation targeting system of claim 1, wherein the interactive display representing the anatomy of the patient is based on actual measured anatomic characteristics of the patient.

9. The neuromodulation targeting system of claim 1, wherein the interactive display further facilitates selection of an exclusion zone of the anatomy of the patient that is to be free of one or more specified types of neuromodulation.

10. The neuromodulation targeting system of claim 1, further comprising:
    an electrotherapy parameter selector engine configured to determine an electrical signal waveform to be applied to the first target region, the electrical signal waveform being specific to a neurologic structure present at the first target region.

11. The neuromodulation targeting system of claim 10, wherein the electrotherapy parameter selector engine is further configured to determine the electrical signal waveform based on an activation function associated with the neurologic structure at the first target region.

12. The neuromodulation targeting system of claim 11, wherein the electrotherapy parameter selector engine is configured to determine the electrical signal waveform based on an orientation of the neurologic structure at the first target region relative to a location of a set of electrodes from which the neuromodulation therapy is to be directed.

13. The neuromodulation targeting system of claim 10, wherein the GUI includes a treatment objective input to accept a clinical effect objective specified by a user; and
    wherein the electrotherapy parameter selector engine is further configured to determine the electrical signal waveform based on the clinical effect objective.

14. The neuromodulation targeting system of claim 1, wherein the first localized clinical effect includes at least one effect selected from the group consisting of: pain relief, paresthesia, natural-touch simulation, or any combination thereof.

15. In a neuromodulation targeting system, a method for facilitating spatial selection of a neuromodulation objective, the method comprising:
    providing a graphical user interface (GUI) that includes an interactive display representing anatomy of a patient with user-selectable anatomic sites associated with a plurality of predefined neural pathways corresponding to distinct localized clinical effects of neuromodulation, wherein the interactive display includes at least one of a dermatomal map of the patient with individually-selectable dermatomes, a spinal map of the patient with selectable portions of dorsal roots, or a map of fiber tracts proximate the spinal cord with selectable portions of the fiber tracts, and wherein the interactive display further includes a therapy type selector input facilitating a user-selection of neuromodulation type for each selected site from the user-selectable anatomic sites, the user-selection of neuromodulation type including a user-selection from among paresthesia neuromodulation and sub-perception neuromodulation; and responding to user selection of a first anatomic site, including:

computationally determining a first target region where neuromodulation therapy is to be directed, the first target region being distinct from an anatomic location corresponding to the user-selected first anatomic site, and configuring the neuromodulation therapy for delivery to the first target region to produce a first localized clinical effect in the patient at the anatomic location corresponding to the user-selected first anatomic site, upon administration of the neuromodulation therapy to the patient, to achieve the neuromodulation objective.

16. The method of claim 15, further comprising:
determining an electrical signal waveform to be applied to the first target region, the electrical signal waveform being specific to a neurologic structure present at the first target region.

17. The method of claim 16, further comprising:
determining the electrical signal waveform based on an activation function associated with the neurologic structure at the first target region.

18. The method of claim 17, further comprising:
determining the electrical signal waveform based on an orientation of the neurologic structure at the first target region relative to a location of a set of electrodes from which the neuromodulation therapy is to be directed.

19. The method of claim 16, wherein the GUI includes a treatment objective input to accept a clinical effect objective specified by a user; further comprising:
determining the electrical signal waveform based on the clinical effect objective.

20. The method of claim 15, wherein the interactive display further facilitates selection of an exclusion zone of the anatomy of the patient that is to be free of one or more specified types of neuromodulation.

* * * * *